(12) United States Patent
Wang et al.

(10) Patent No.: US 11,478,321 B2
(45) Date of Patent: Oct. 25, 2022

(54) SEAL INTEGRITY INDICATORS FOR STERILIZATION CONTAINERS

(71) Applicant: O&M Halyard, Inc., Mechanicsville, VA (US)

(72) Inventors: Ruoya Wang, Decatur, GA (US); Anthony Stephen Spencer, Woodstock, GA (US); Kun-Chi Wu, Johns Creek, GA (US); Tracy J. White, Cumming, GA (US); Edward B. Madsen, Cumming, GA (US); Justin J. Coker, Laguna Niguel, CA (US); Nathan C. Griffith, Johns Creek, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 269 days.

(21) Appl. No.: 16/524,654

(22) Filed: Jul. 29, 2019

(65) Prior Publication Data
US 2020/0039719 A1 Feb. 6, 2020

Related U.S. Application Data

(60) Provisional application No. 62/757,845, filed on Nov. 9, 2018, provisional application No. 62/712,287, filed on Jul. 31, 2018.

(51) Int. Cl.
*B65D 51/24* (2006.01)
*A61B 50/30* (2016.01)
*B65D 81/20* (2006.01)

(52) U.S. Cl.
CPC ............ *A61B 50/30* (2016.02); *B65D 51/245* (2013.01); *B65D 81/2015* (2013.01); *B65D 81/2038* (2013.01); *B65D 2203/12* (2013.01)

(58) Field of Classification Search
CPC . A61B 50/30; A61B 50/34; A61B 2050/3011; A65D 51/245; A65D 79/005;
(Continued)

(56) References Cited

U.S. PATENT DOCUMENTS

| 3,527,400 A | 9/1970 | Shepherd et al. |
| 3,730,338 A | 5/1973 | Chesky |

(Continued)

FOREIGN PATENT DOCUMENTS

| CN | 103480022 A | 1/2014 |
| JP | 2005230436 A | 9/2005 |

(Continued)

OTHER PUBLICATIONS

International Search Report and Written Opinion for PCT/IB2019/056451, dated Jan. 7, 2020, 14 pages.

*Primary Examiner* — Steven A. Reynolds
(74) *Attorney, Agent, or Firm* — Dority & Manning, P.A.

(57) ABSTRACT

Indicators for indicating the integrity of a seal of a sterilization container are provided. For example, a seal indicator may indicate whether the container is sufficiently sealed to prevent an ingress of contaminants into the container. If the container is sufficiently sealed, the seal indicator is in one state and displays a first indicium, and if the sterilization container is not sufficiently sealed, the seal indicator is in another state and displays a second indicium. Thus, the seal indicator undergoes a visible change in state when the sterilization container transitions from unsealed to sealed, such that the user may be assured that the container is properly sealed to maintain sterility of the articles post-sterilization. Further, the seal indicator undergoes a visible change in state if the seal is subsequently broken, to signal to the user that the seal and the sterility of the container interior has been compromised.

19 Claims, 23 Drawing Sheets

(58) Field of Classification Search
CPC .......... A65D 2203/12; A65D 81/2038; B65D 51/245; B65D 79/005; B65D 2203/12; B65D 81/2038
USPC ...................................................... 206/459.1
See application file for complete search history.

(56) References Cited

U.S. PATENT DOCUMENTS

| | | | |
|---|---|---|---|
| 4,193,496 A | | 3/1980 | Barratt |
| 4,299,921 A | * | 11/1981 | Youssef ................. C12M 23/10 435/305.4 |
| 4,349,118 A | | 9/1982 | Sanderson et al. |
| 4,466,552 A | | 8/1984 | Butterworth et al. |
| 4,489,841 A | * | 12/1984 | Thompson ........... B65D 55/026 215/203 |
| 4,551,311 A | | 11/1985 | Lorenz |
| 4,562,047 A | | 12/1985 | Sestak et al. |
| 4,643,303 A | | 2/1987 | Arp et al. |
| 4,671,943 A | | 6/1987 | Wahlquist |
| 4,706,839 A | | 11/1987 | Spence |
| 4,774,063 A | | 9/1988 | Runnells |
| 4,915,913 A | | 4/1990 | Williams et al. |
| 4,919,888 A | * | 4/1990 | Spence ..................... A61L 2/26 422/26 |
| 5,115,929 A | | 5/1992 | Buono |
| 5,147,351 A | | 9/1992 | Wagner |
| 5,217,698 A | | 6/1993 | Siegel et al. |
| 5,372,787 A | | 12/1994 | Ritter |
| 5,407,069 A | | 4/1995 | Schmieding et al. |
| 5,427,266 A | * | 6/1995 | Yun ......................... B65D 25/54 116/200 |
| 5,573,741 A | | 11/1996 | Riley |
| 5,641,065 A | | 6/1997 | Owens et al. |
| 5,887,745 A | | 3/1999 | Wood |
| 6,010,670 A | | 1/2000 | Berry, Jr. |
| 6,099,812 A | | 8/2000 | Allen et al. |
| 6,189,551 B1 | | 2/2001 | Sargent et al. |
| 6,207,100 B1 | | 3/2001 | Weiss et al. |
| 6,247,609 B1 | | 6/2001 | Gabele et al. |
| 6,311,838 B1 | | 11/2001 | Johnson et al. |
| 6,350,418 B1 | | 2/2002 | Venderpool et al. |
| 6,589,477 B1 | | 7/2003 | Frieze et al. |
| 6,669,360 B1 | | 12/2003 | Adelmann et al. |
| 6,755,207 B1 | | 6/2004 | Curtis et al. |
| 6,893,158 B1 | | 5/2005 | Tipp et al. |
| 7,106,202 B2 | | 9/2006 | Dickinson |
| 8,435,445 B2 | | 5/2013 | Kral |
| 8,623,289 B2 | | 1/2014 | Cesa et al. |
| 8,763,839 B2 | | 7/2014 | Sakairi |
| 8,815,174 B2 | | 8/2014 | Bacik et al. |
| 8,899,443 B2 | | 12/2014 | Soibel et al. |
| 9,028,147 B2 | | 5/2015 | Schmal et al. |
| 9,111,425 B2 | | 8/2015 | Holloway et al. |
| 9,125,727 B2 | | 9/2015 | Dallafior |
| 9,572,905 B2 | | 2/2017 | Schulz et al. |
| 9,610,126 B2 | | 4/2017 | Griffin |
| 2001/0032850 A1 | | 10/2001 | Neuner |
| 2004/0197248 A1 | | 10/2004 | Hasegawa et al. |
| 2006/0000733 A1 | | 1/2006 | Albritton et al. |
| 2009/0266818 A1 | | 10/2009 | Sauvageau |
| 2012/0211493 A1 | | 8/2012 | Daggett |
| 2013/0280134 A1 | | 10/2013 | Hoffman et al. |
| 2015/0327934 A1 | | 11/2015 | Thomas et al. |
| 2015/0368009 A1 | | 12/2015 | Loukov |
| 2016/0083150 A1 | | 3/2016 | Diminick et al. |
| 2016/0108566 A1 | | 4/2016 | Tseng et al. |
| 2016/0194126 A1 | | 7/2016 | Findlay |
| 2016/0263264 A1 | | 9/2016 | Schulz et al. |
| 2018/0105334 A1 | | 4/2018 | Carver et al. |

FOREIGN PATENT DOCUMENTS

| | | |
|---|---|---|
| WO | WO 2008/078169 A2 | 7/2008 |
| WO | WO 2015/017828 A1 | 2/2015 |
| WO | WO 2019/006079 A2 | 1/2019 |

\* cited by examiner

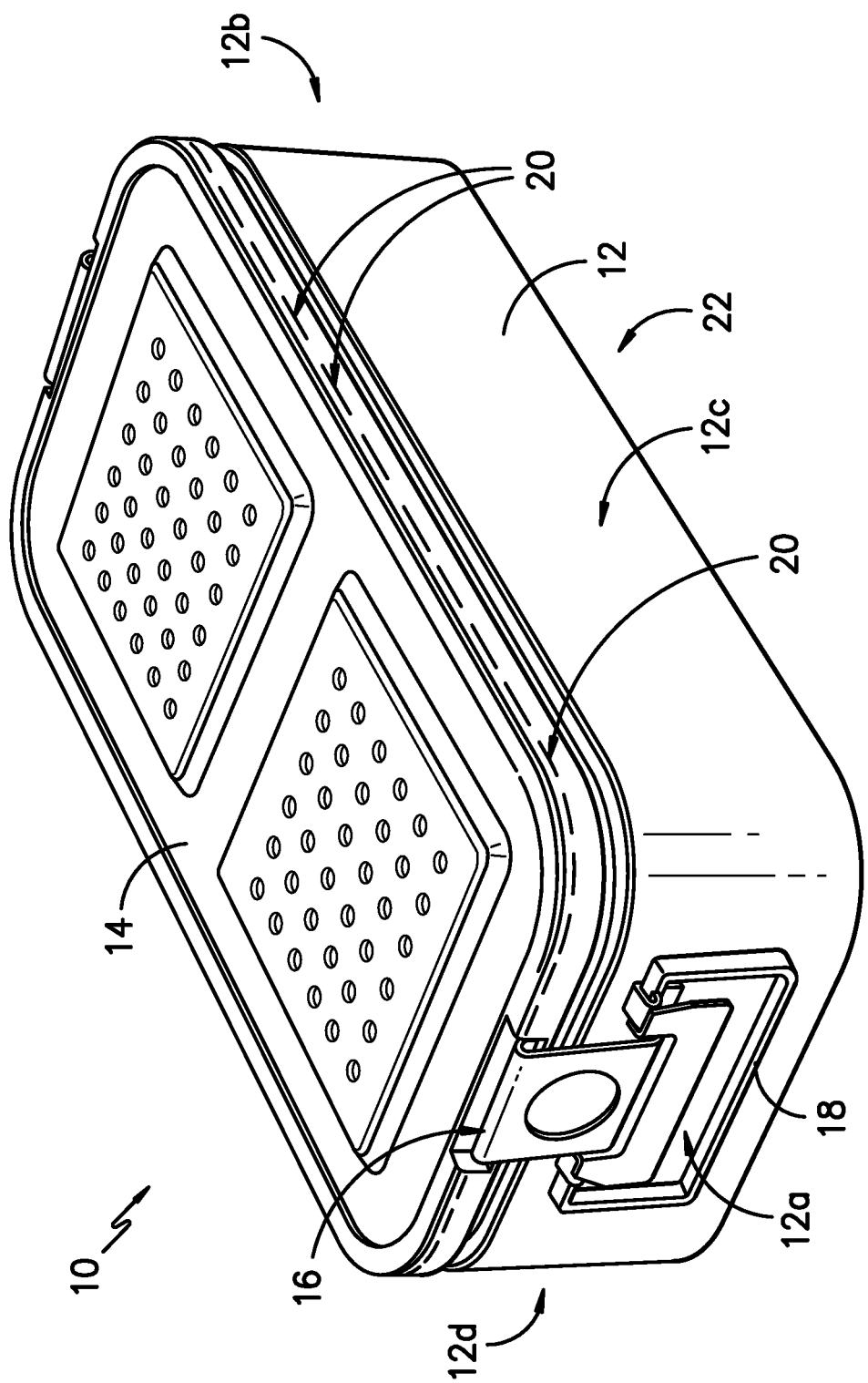
FIG. -1-

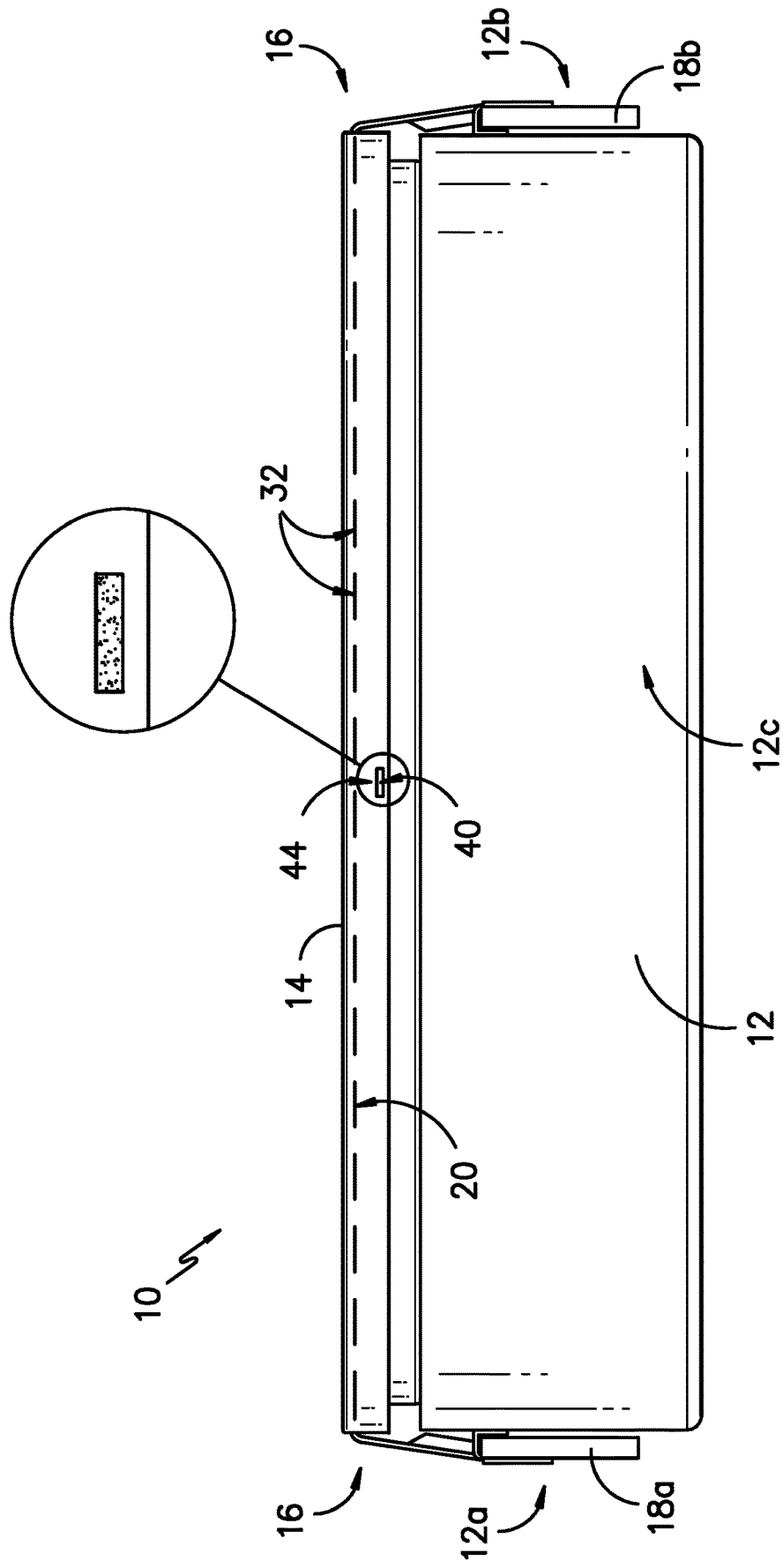

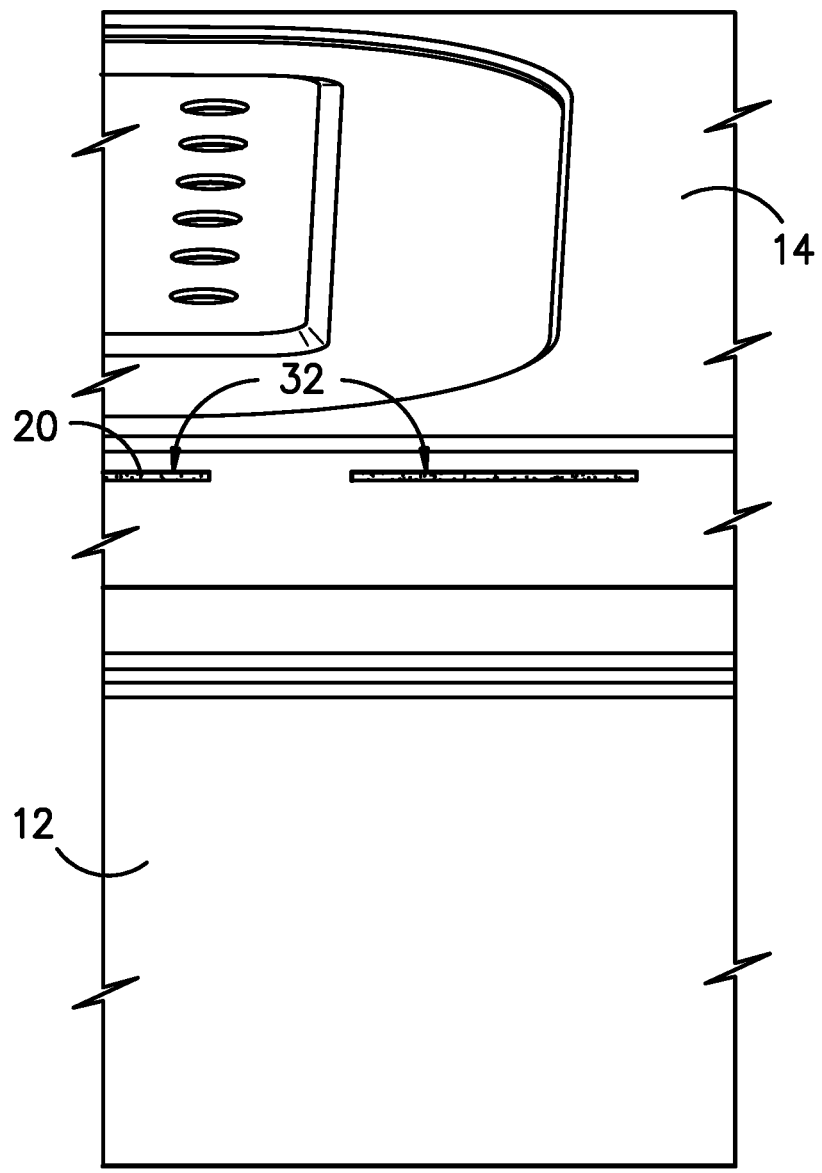
FIG. -3-

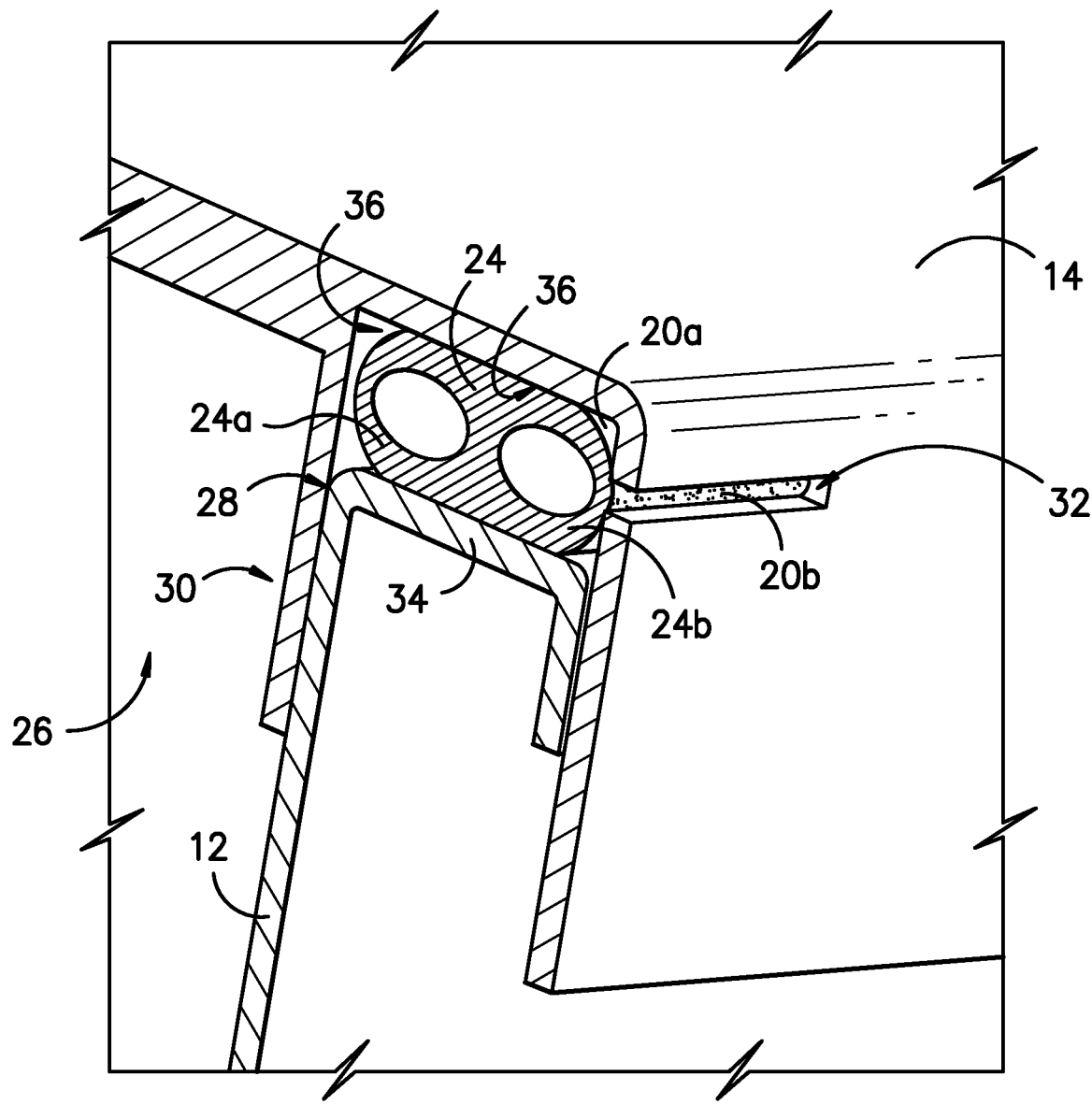
FIG. -4-

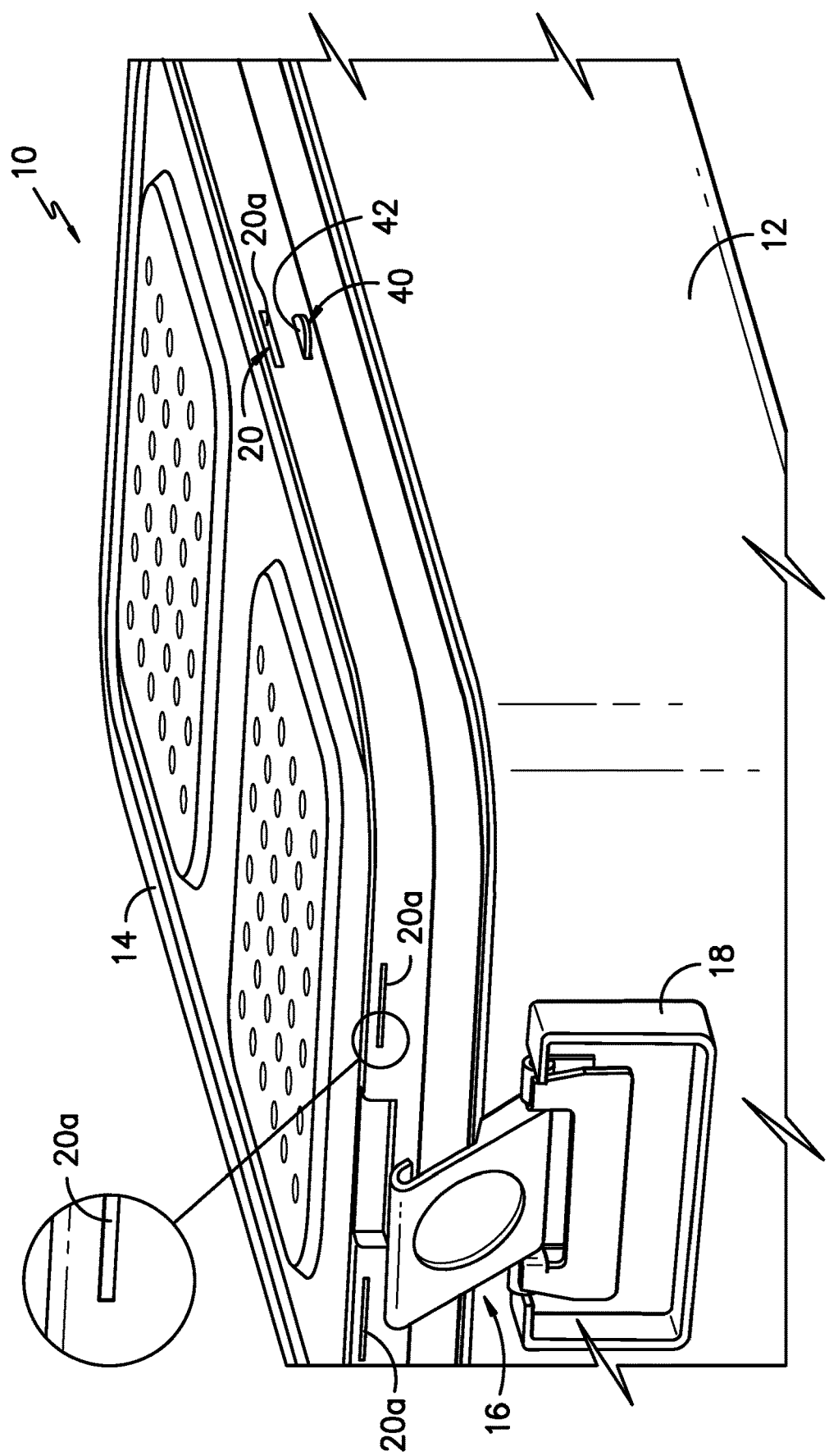

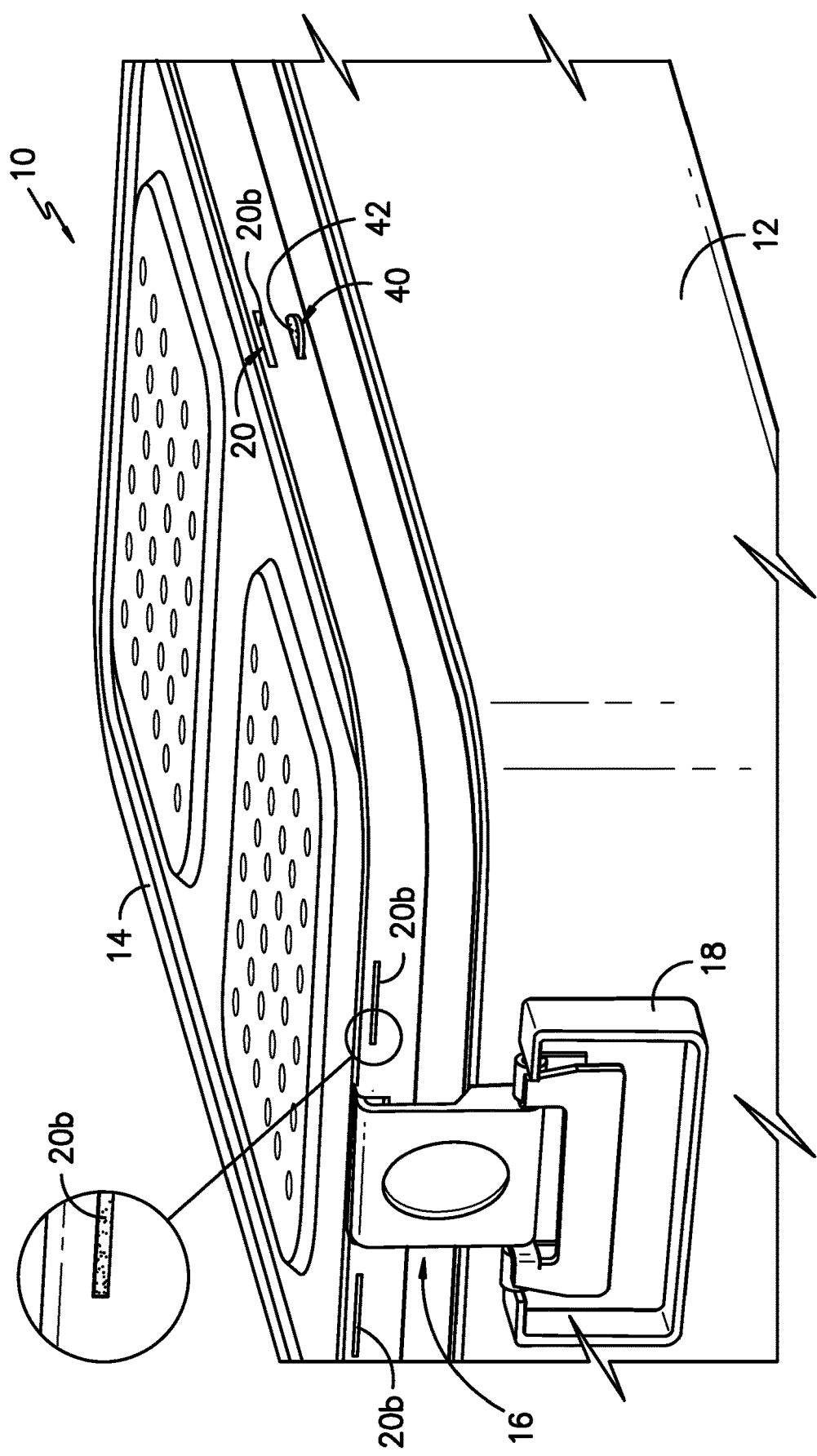
FIG. -6-

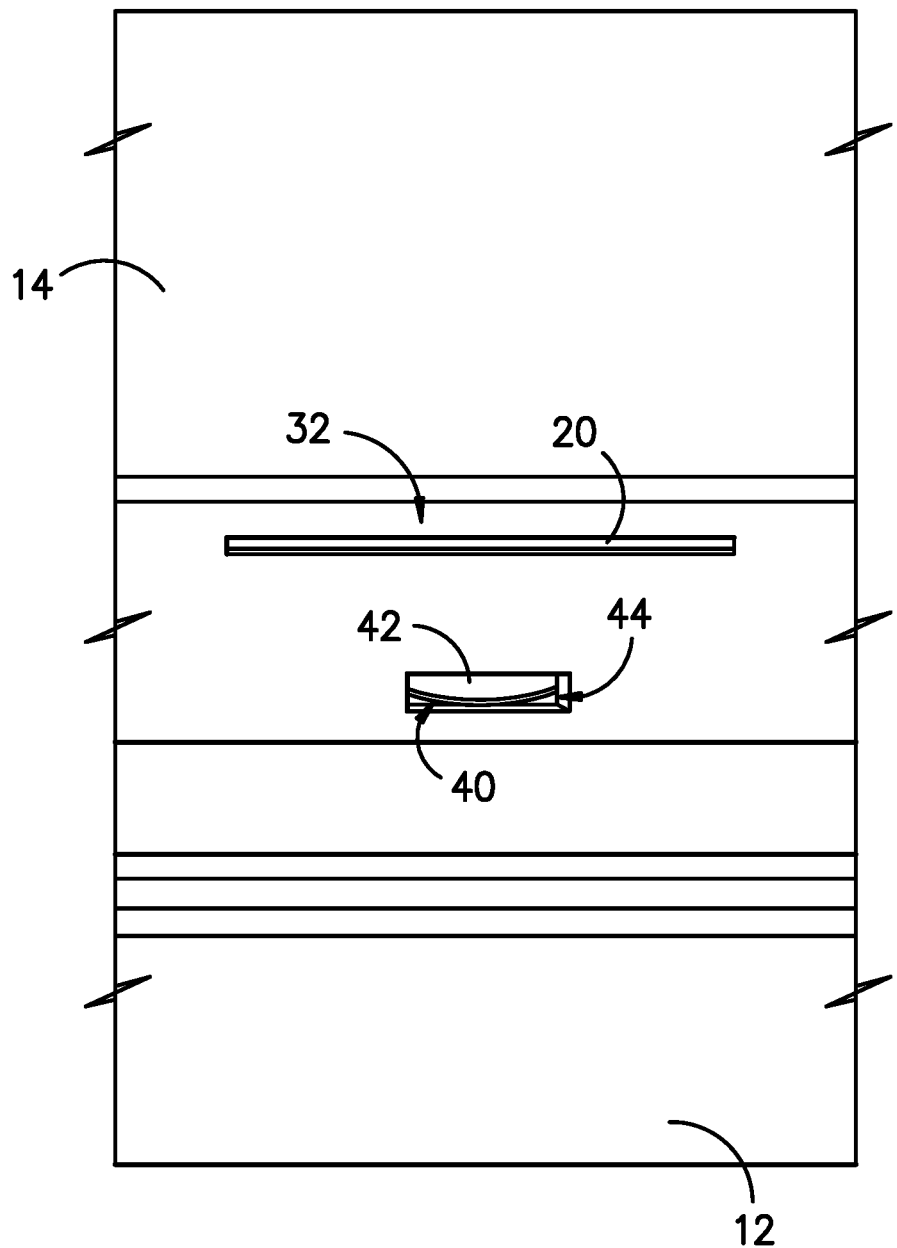
FIG. -7-

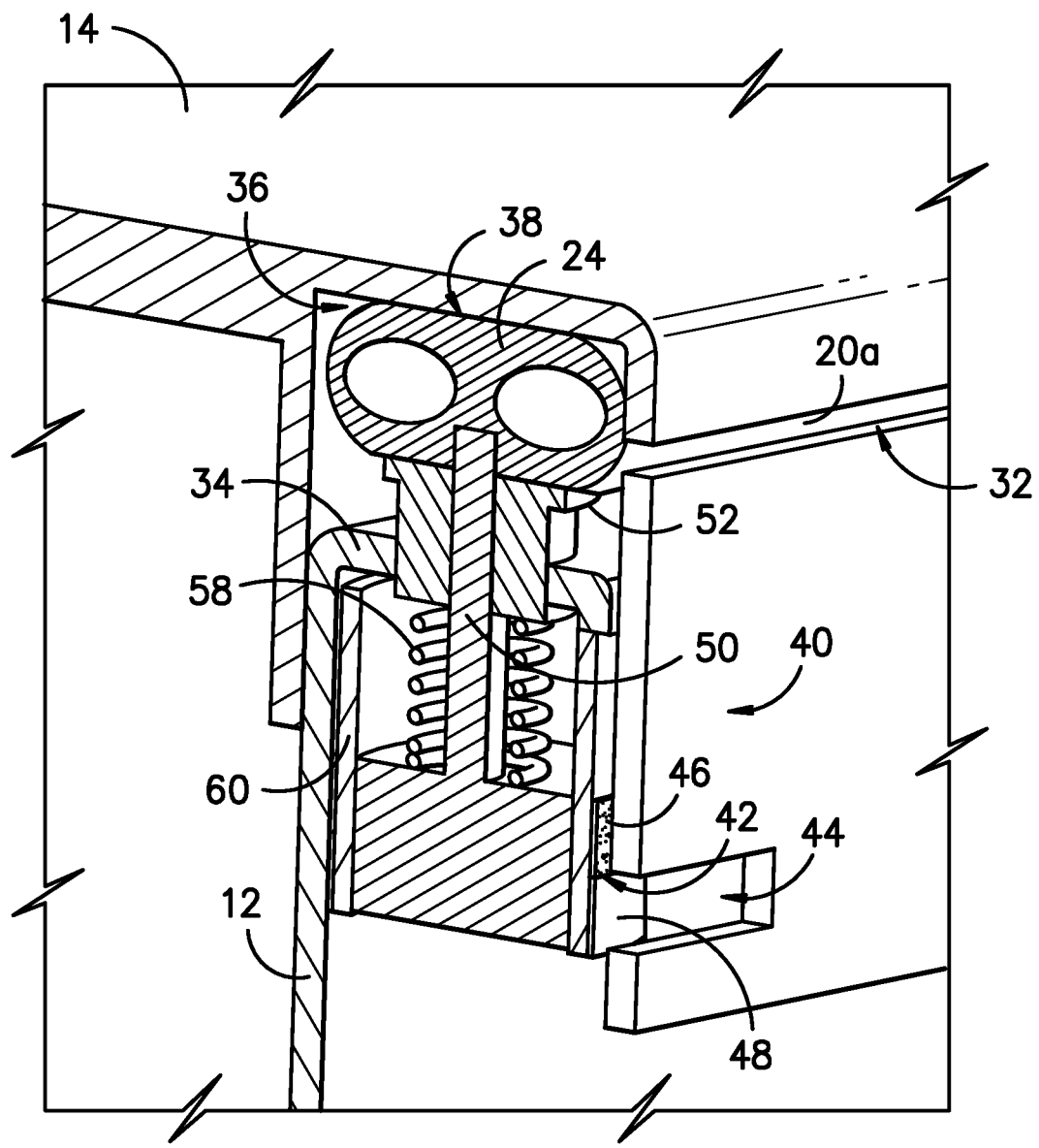
FIG. -8-

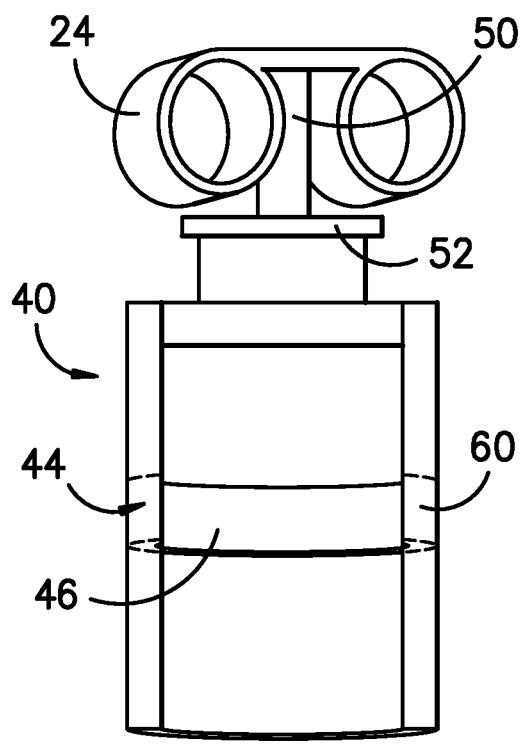
FIG. -9A-
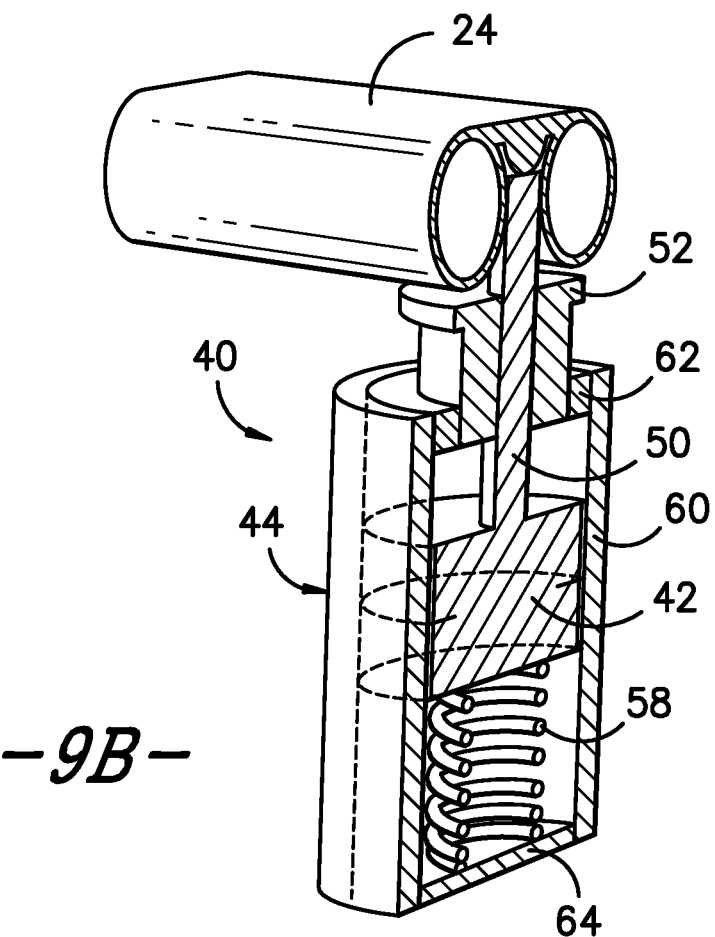
FIG. -9B-

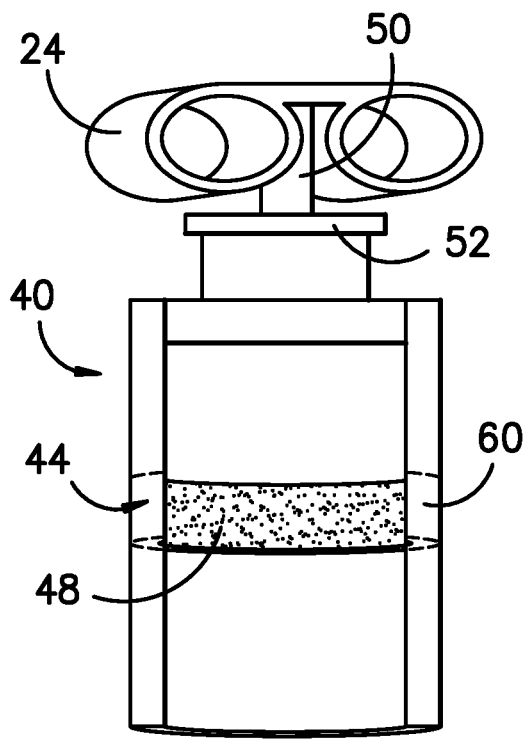
FIG. -10A-
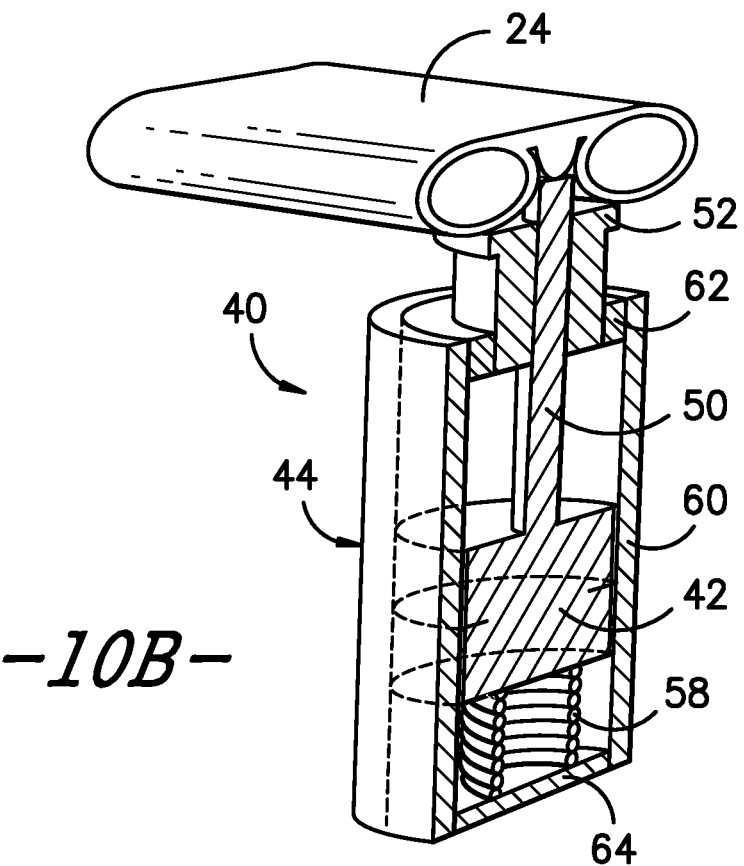
FIG. -10B-

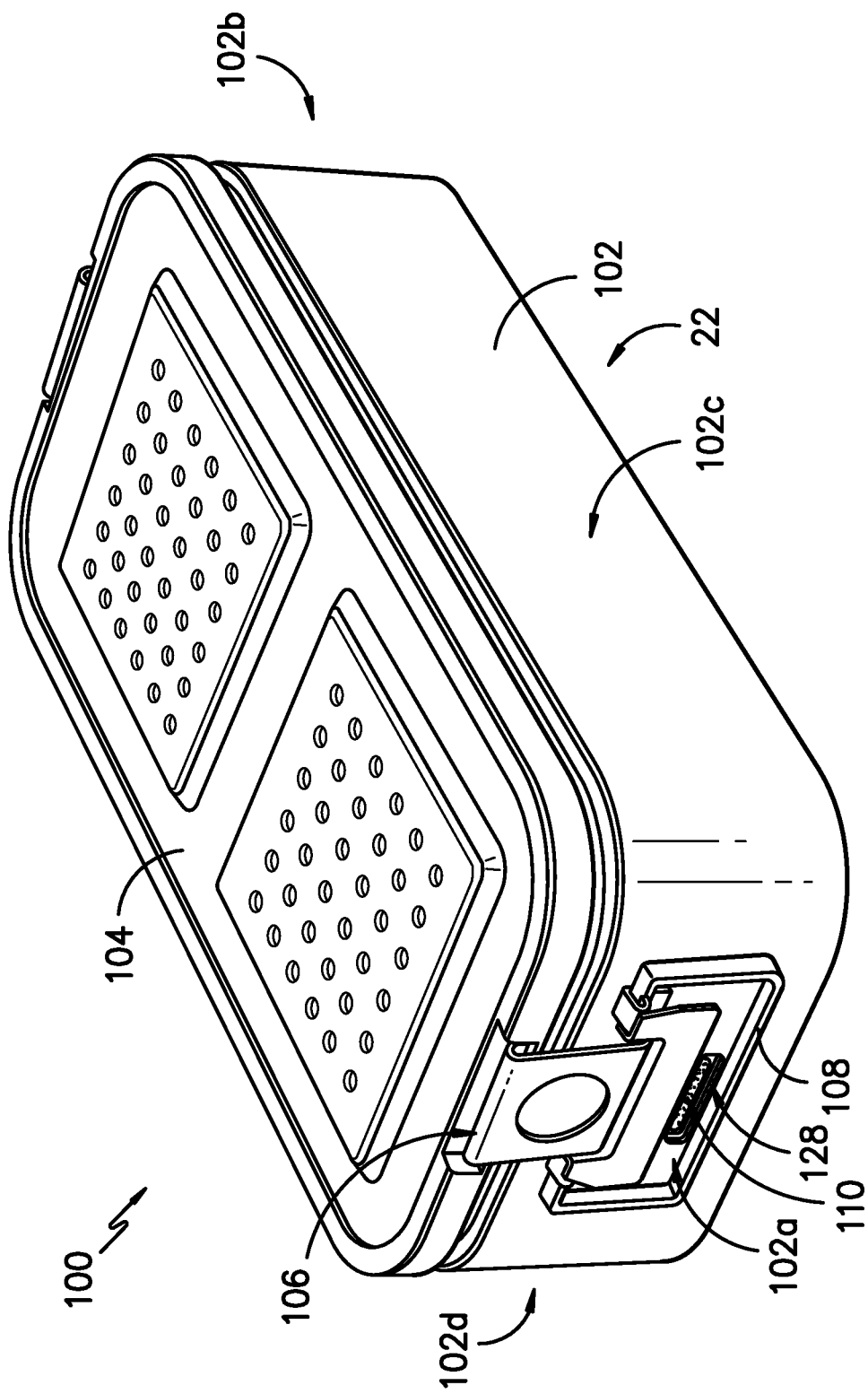
FIG. -11-

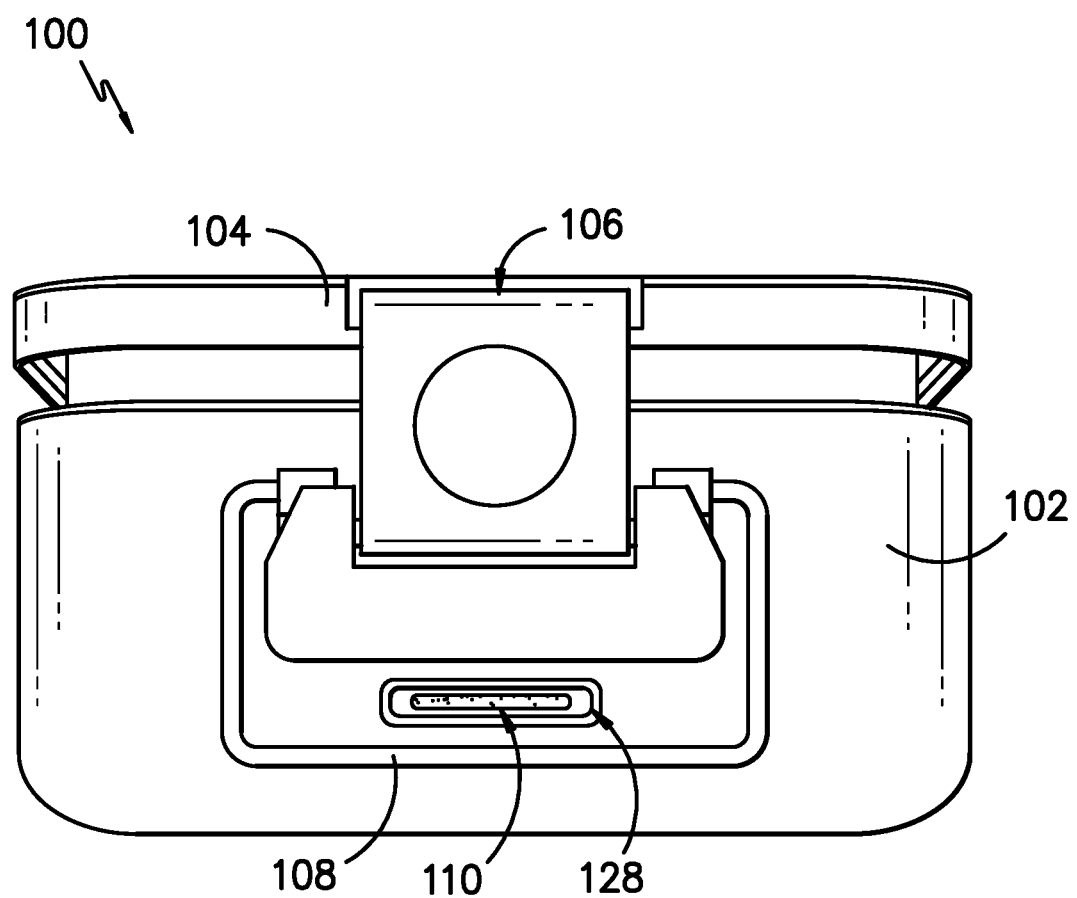
FIG. -12-

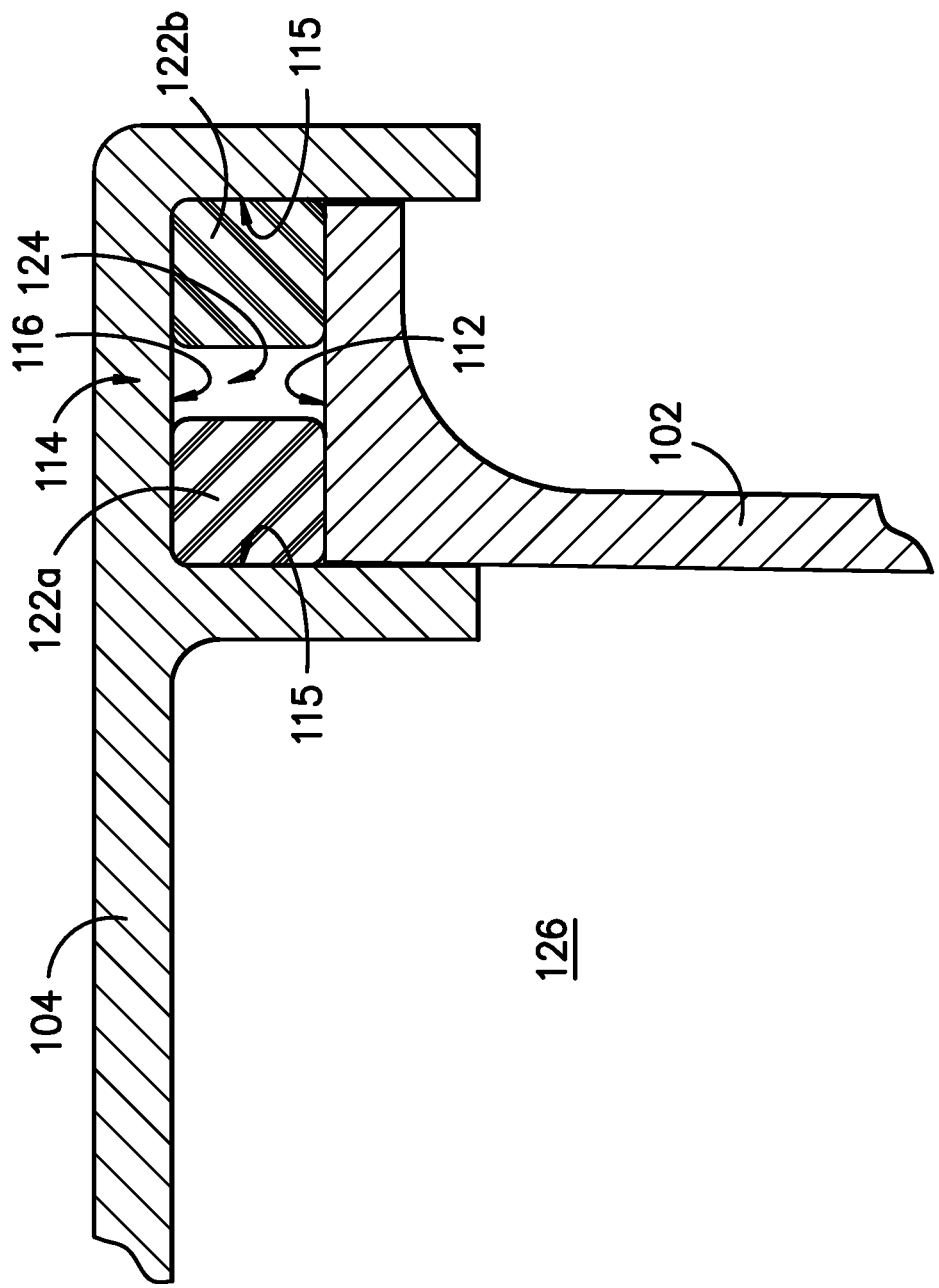

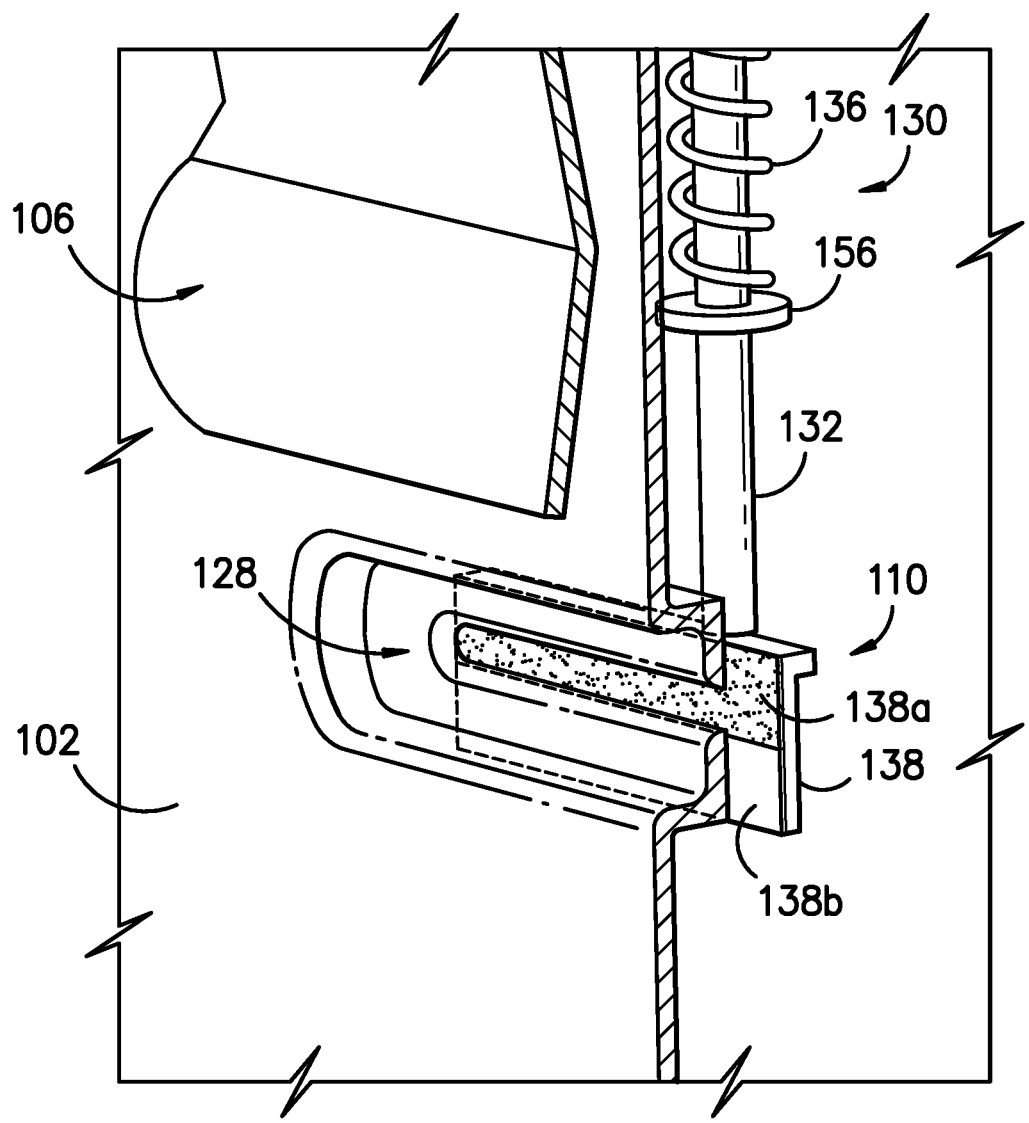
FIG. -14-

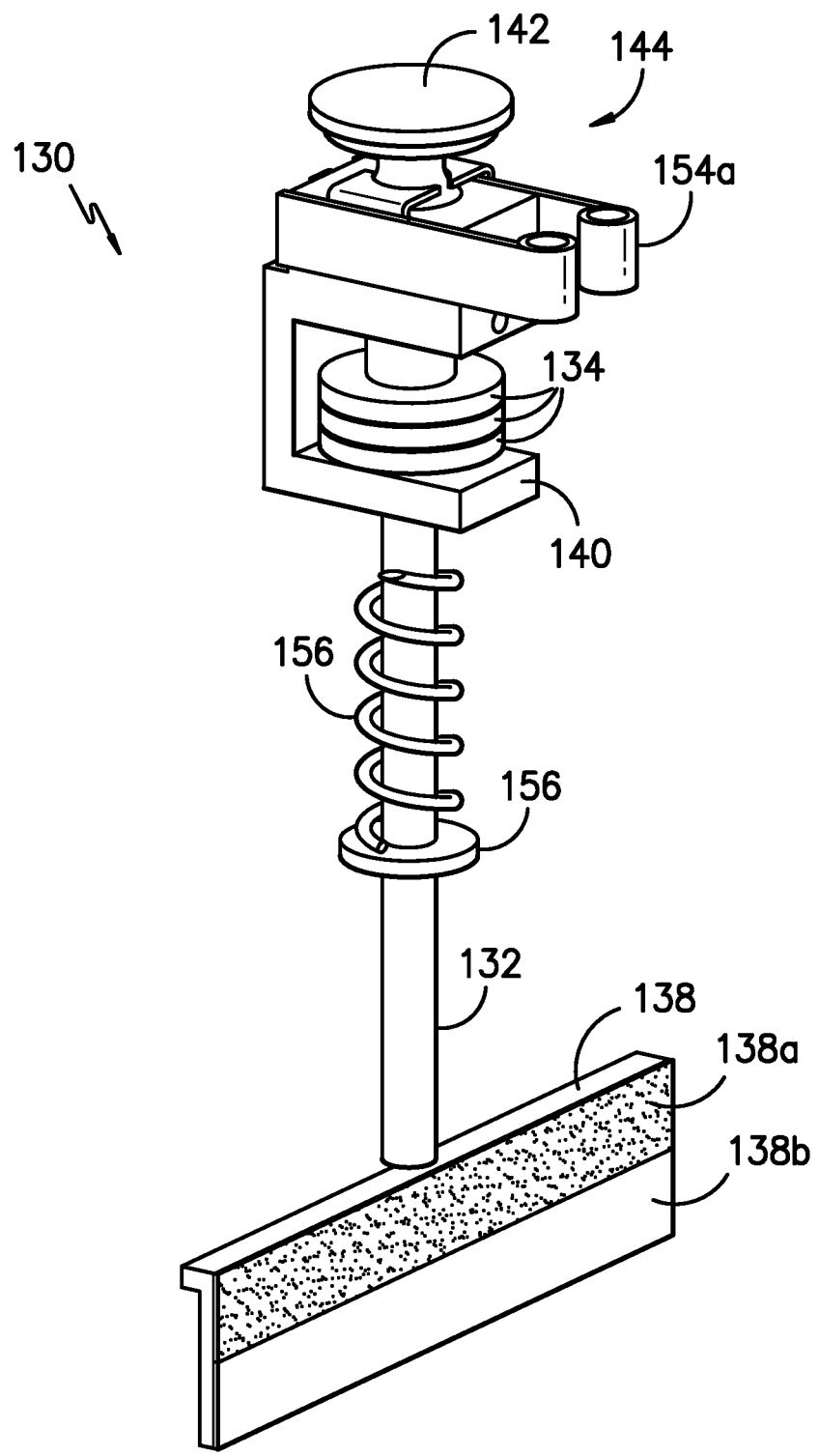
FIG. -15-

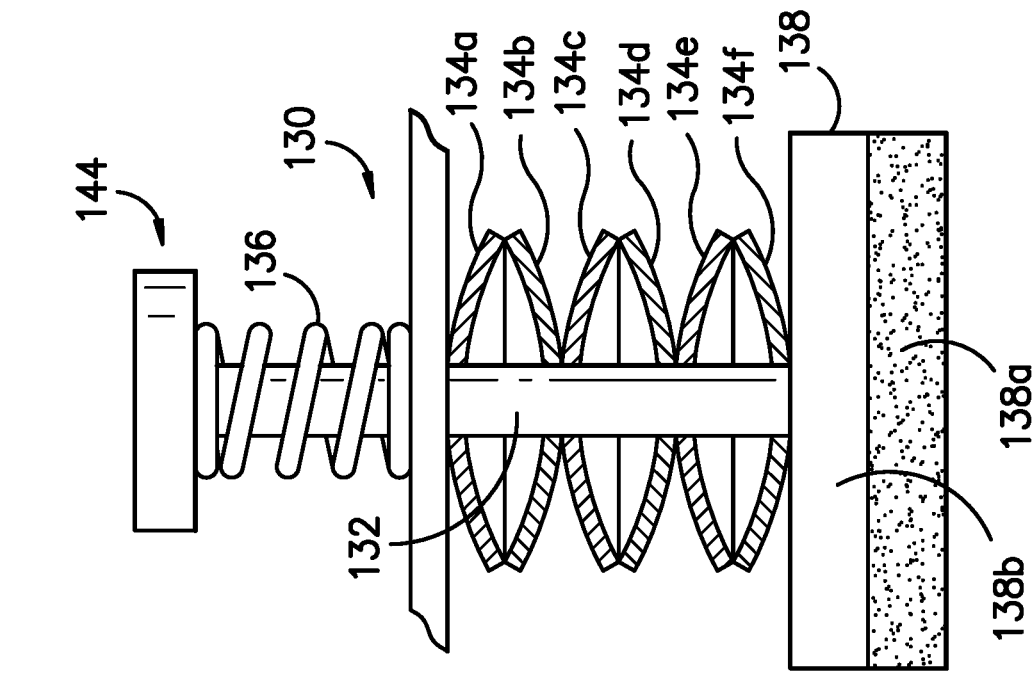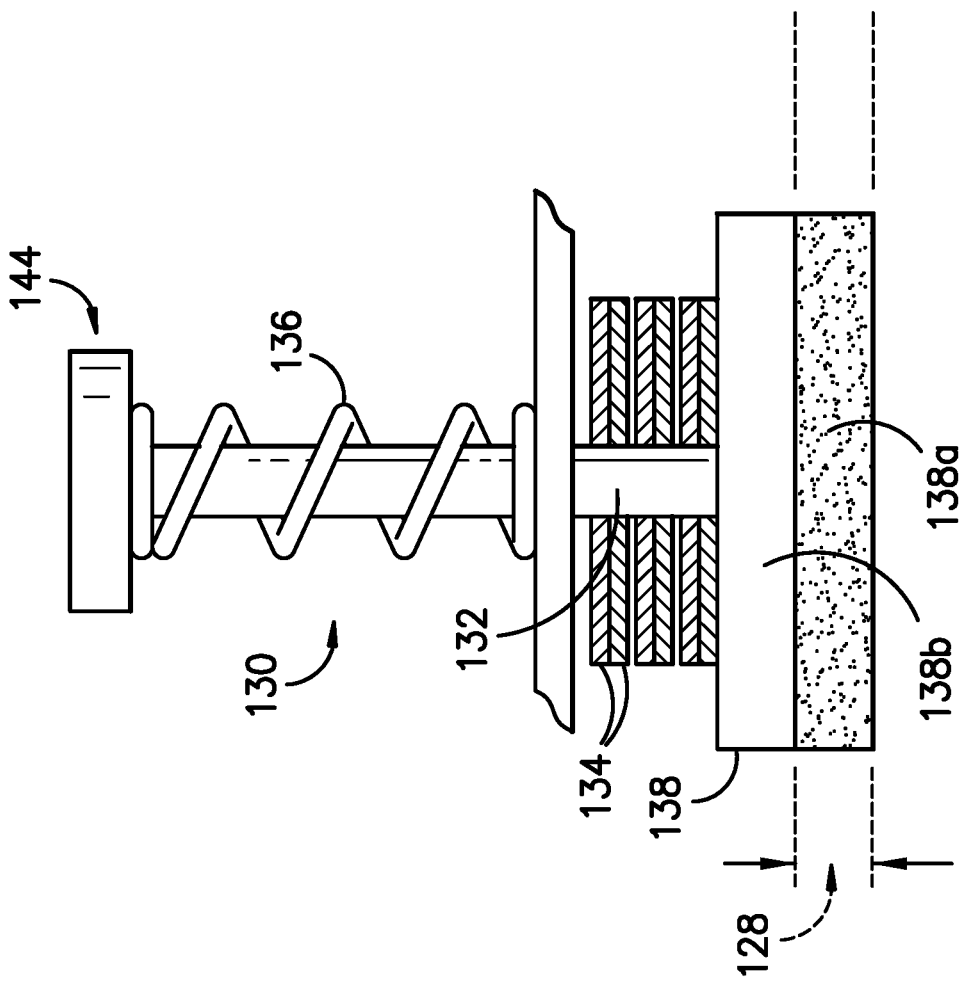

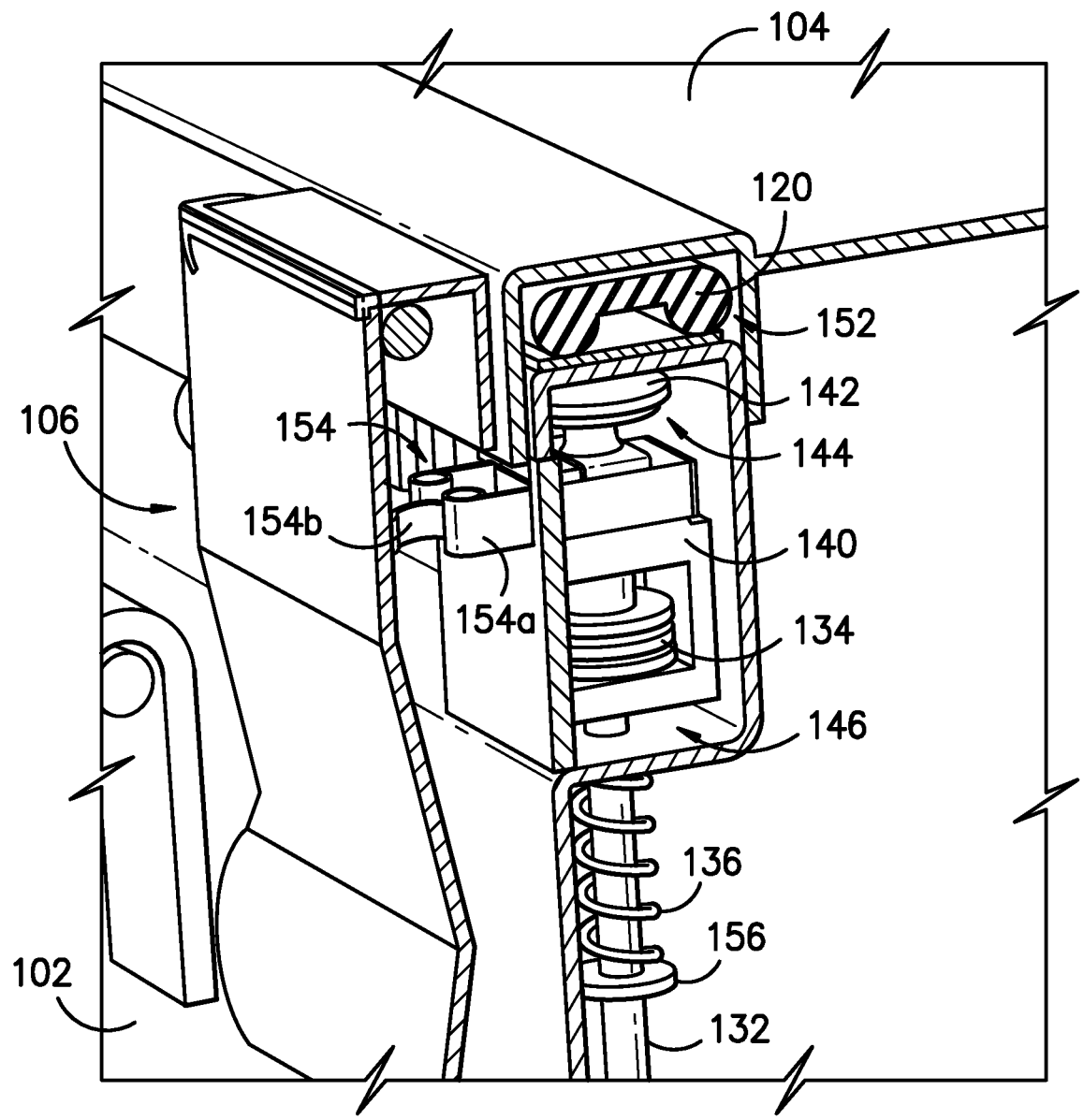
FIG. -17-

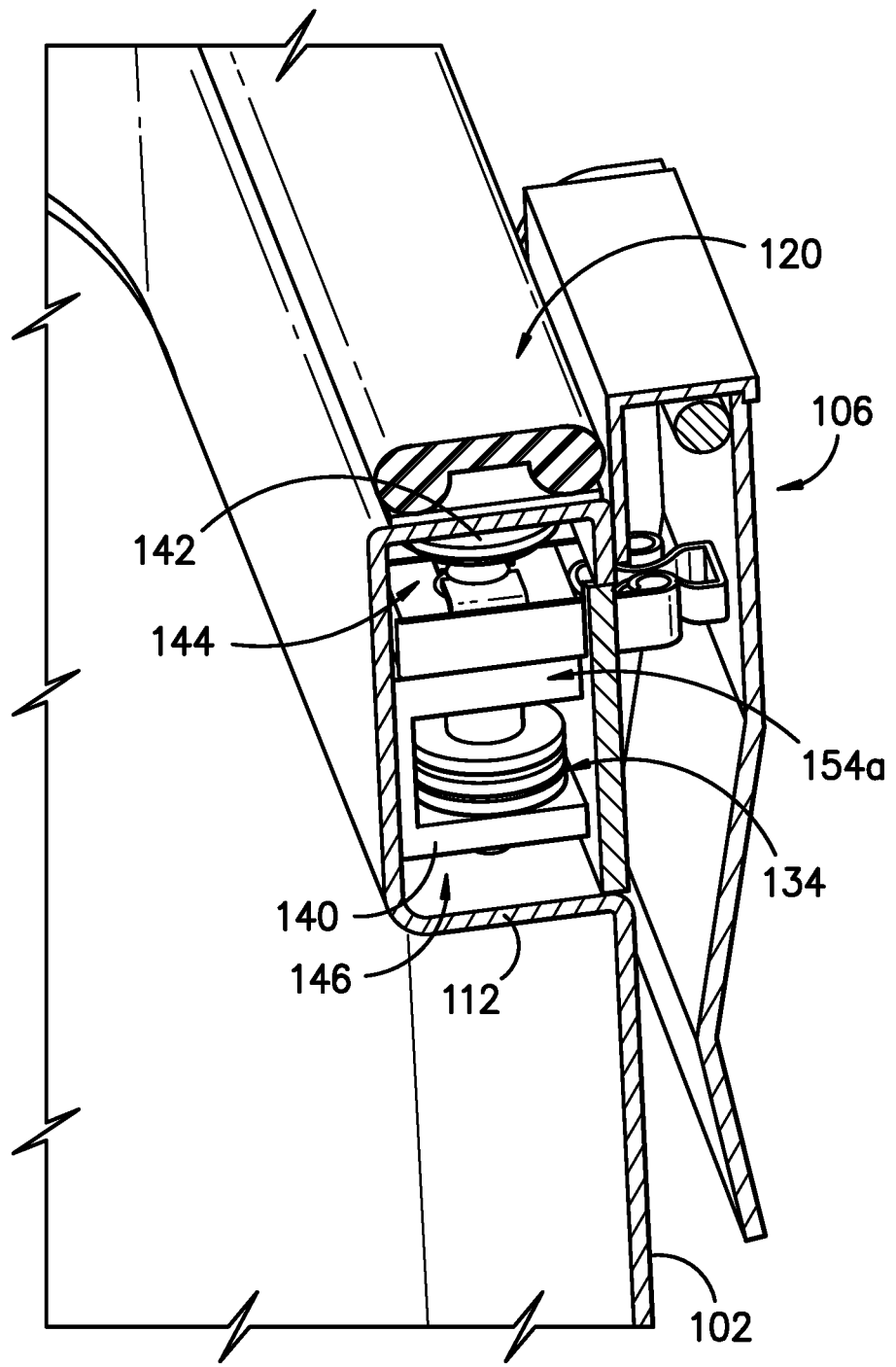
FIG. -18-

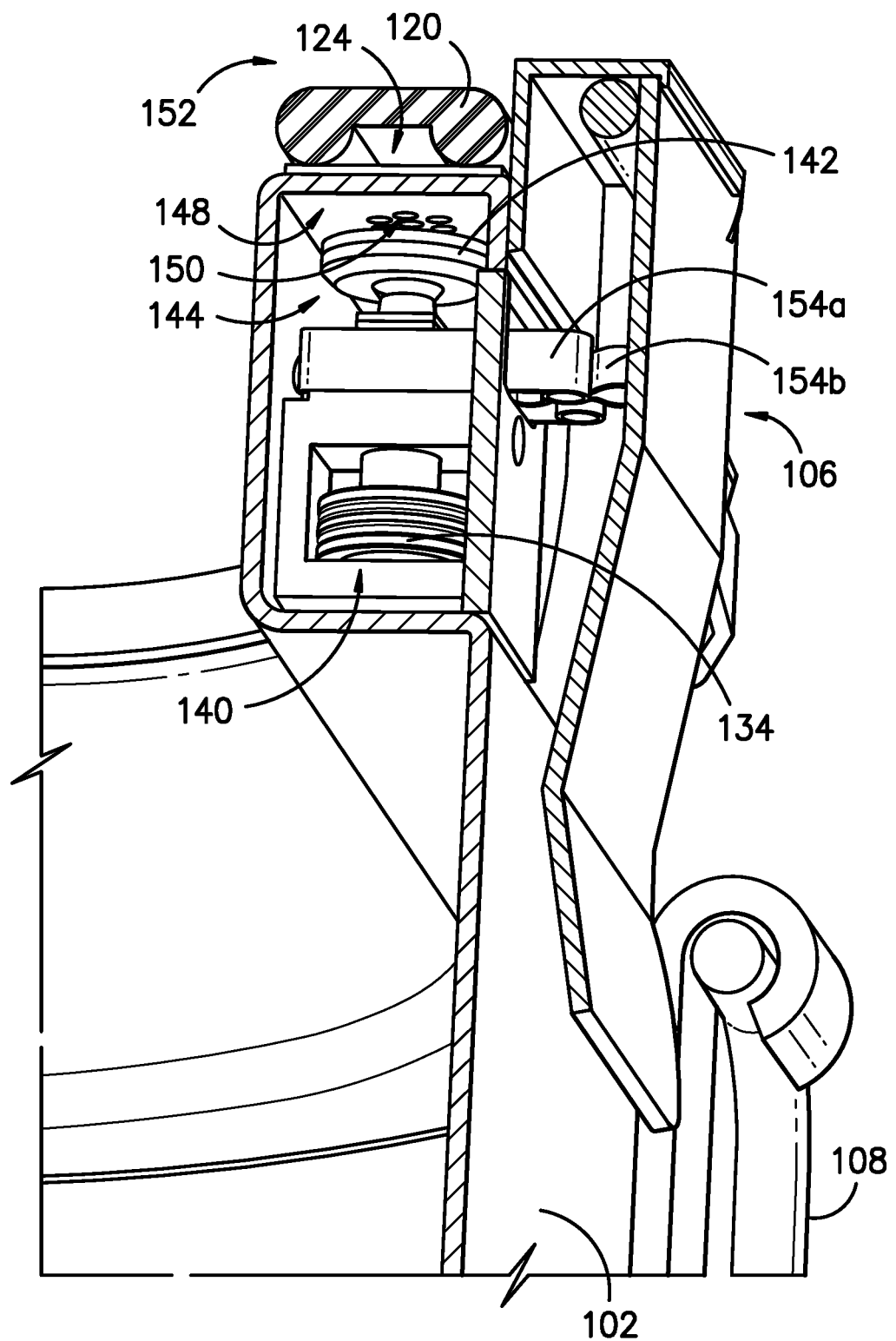
FIG. -19-

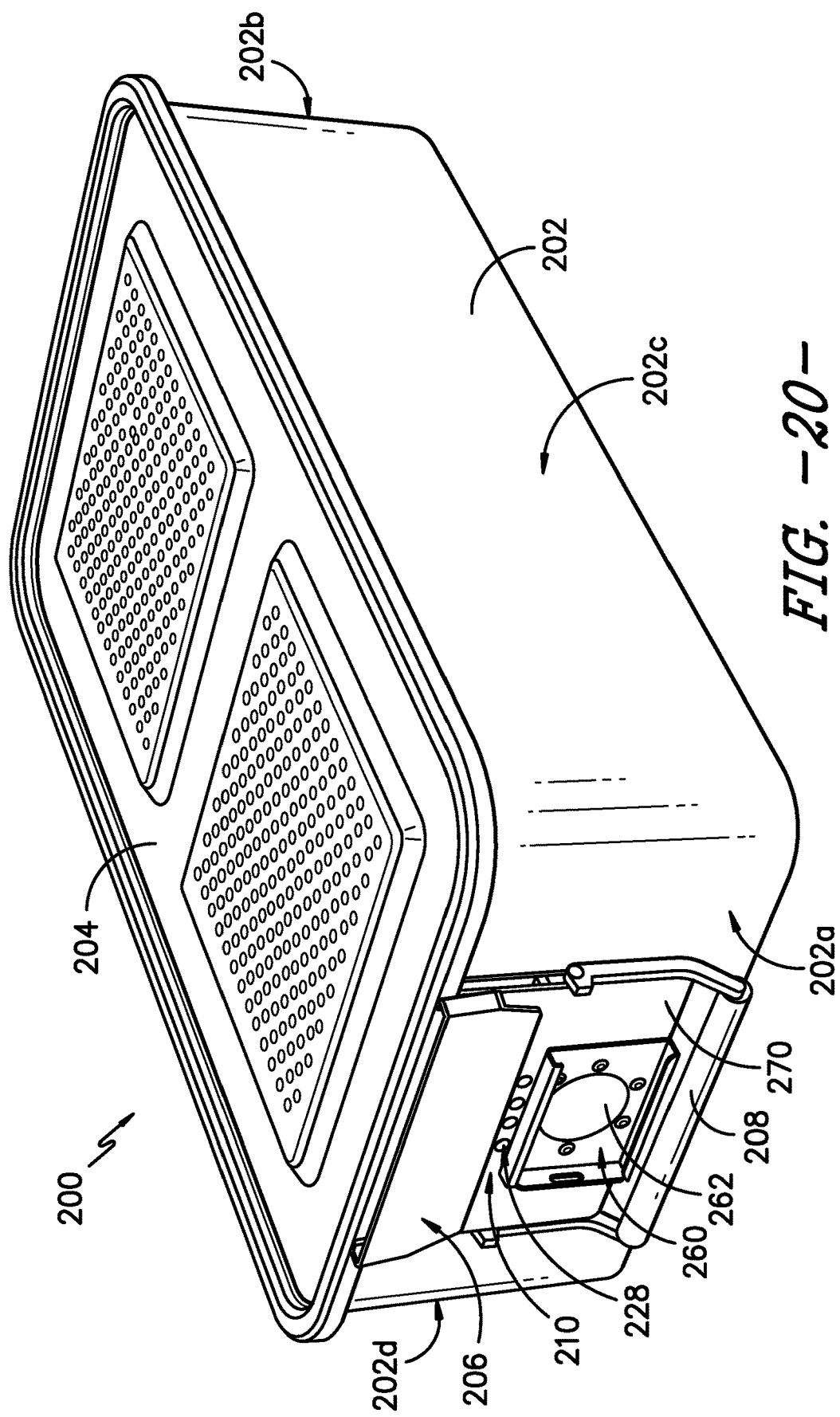
FIG. -20-

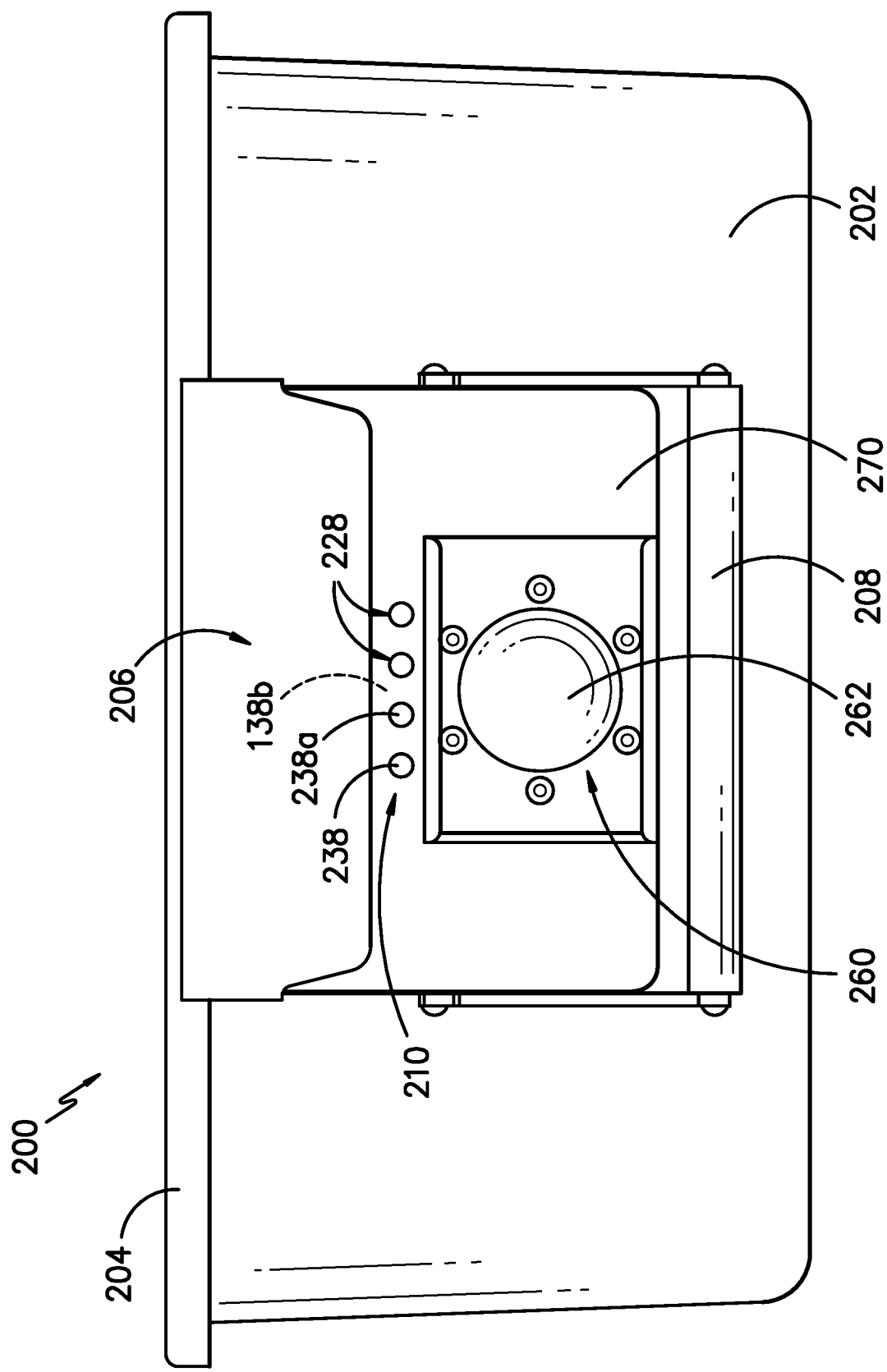

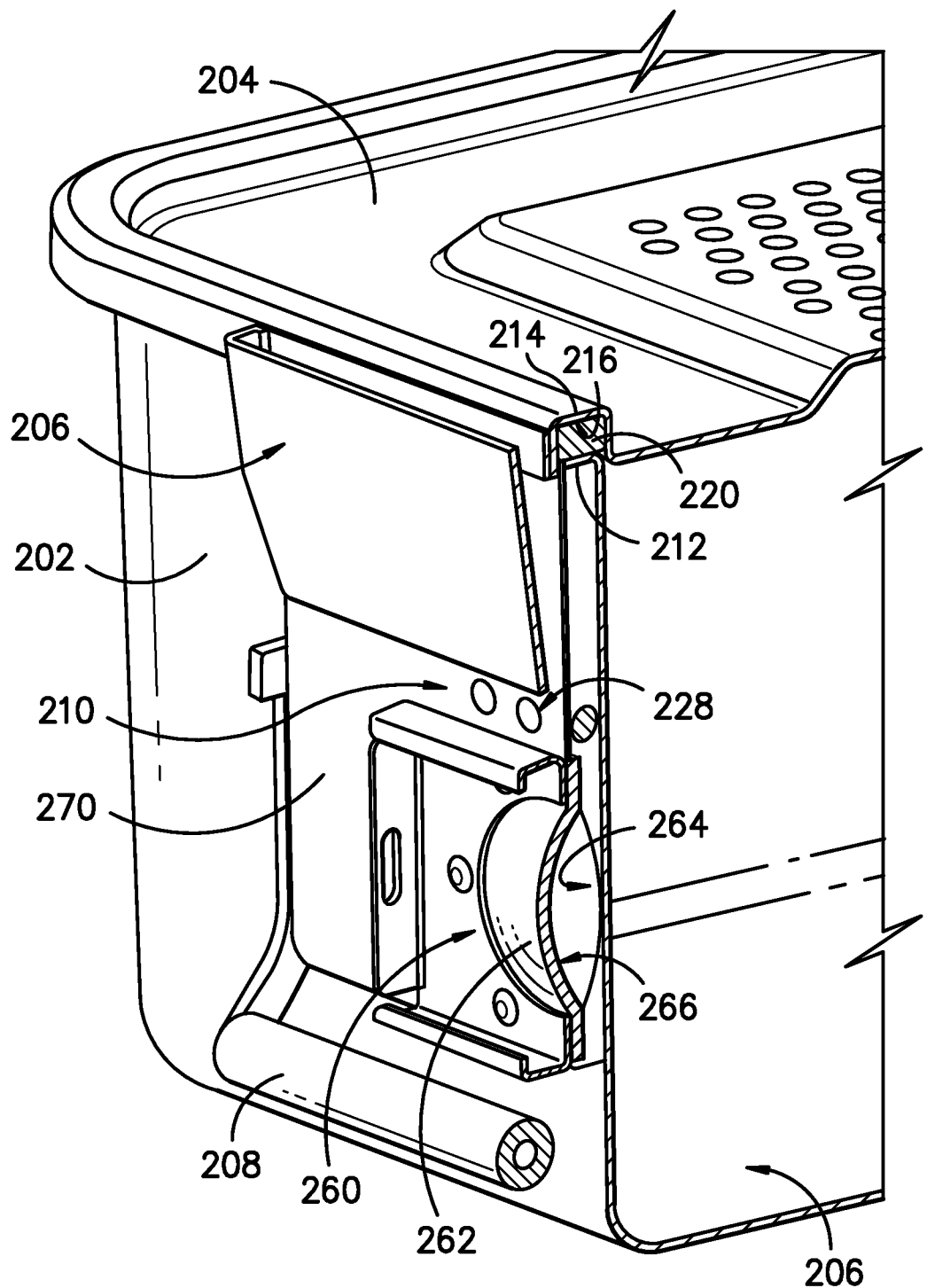
FIG. -22-

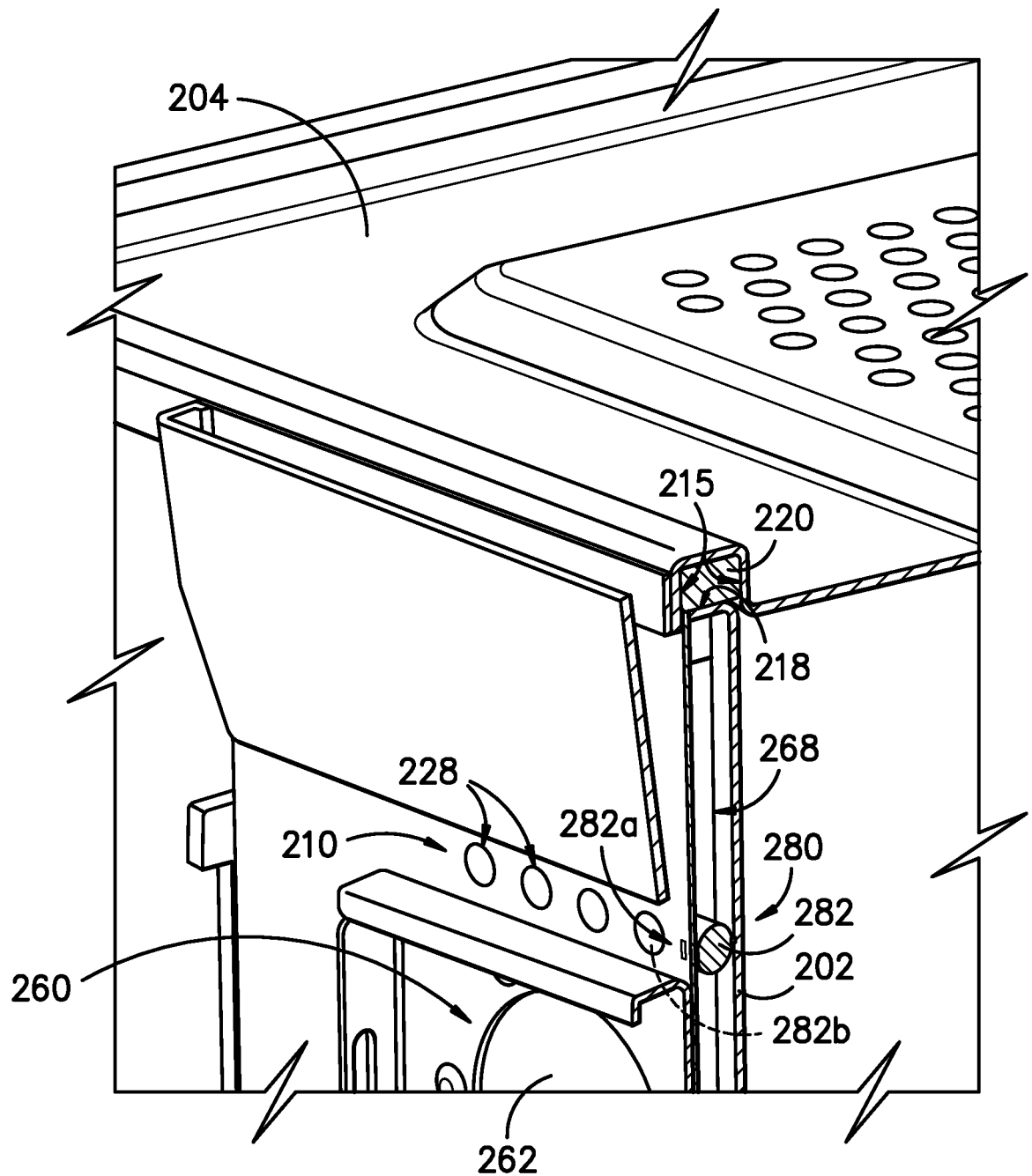
FIG. -23-

SEAL INTEGRITY INDICATORS FOR STERILIZATION CONTAINERS

CROSS-REFERENCE TO RELATED APPLICATIONS

This application claims priority to U.S. Provisional Application Ser. No. 62/712,287, filed Jul. 31, 2018, and U.S. Provisional Application Ser. No. 62/757,845, filed Nov. 9, 2018, the contents of both of which are incorporated herein by reference.

FIELD

The subject matter of the present disclosure relates generally to sterilization containers and, more particularly, to rigid sterilization containers with features for indicating that the sterilization container is properly sealed.

BACKGROUND

Personnel in a sterilization station, such as the Central Service Room (CSR) or the Sterile Processing Department (SPD) of hospitals, are commonly charged with the responsibility of packaging surgical supplies to ensure that the sterility of the packaged contents is maintained from sterilization to the point of reuse. Several activities are involved in the task of sterile supply delivery to the operating room and other units, such as a cardiac catheterization lab, emergency room, labor and delivery room, intensive care unit, pediatric care unit, specialized burn care units, and other surgical or medical units.

Many of the surgical instruments and supplies used in an operating room (OR), or other surgical or medical unit, are reusable. These supplies typically include such things as clamps, scalpel blade handles, retractors, forceps, scissors, surgeon's towels, basins, and the like. All of these supplies must be collected after each procedure, decontaminated, washed and dried before placing into a sterilization packaging system, and sterilized before they can be used again in another procedure. The sterilization packaging systems used must be of the size and shape to accommodate the items to be sterilized, must be compatible with and withstand the physical conditions of the cleaning, disinfection, and sterilization modality processes, and must be capable of maintaining the sterility of their contents post-sterilization.

Typical means of sterilizing surgical instruments, medical devices or accessories include, among others, steam sterilization (e.g., a dynamic-air-removal type such as a prevaccum cycle or steam-flush pressure-pulse (SFPP) cycle), exposure to ethylene oxide gas, and exposure to hydrogen peroxide plasma, as is done with the STERRAD® Sterilization System from Advanced Sterilization Products, Irvine, Calif. or as done with AMSCO V-PRO® Low Temperature Sterilization Systems using Vaporized Hydrogen Peroxide (VHP®) from STERIS. After the sterile barrier system and its contents have been sterilized, the sterilization sterile barrier system typically is stored until it is needed for a surgical procedure, or in some cases may be use immediately.

Common sterile barrier systems, also known as sterilization packaging systems, include sealable pouches, sterilization wraps, and rigid containers. Although each of these systems has some advantage compared to other systems, each of these typical packaging systems also has drawbacks. As an example, a rigid sterilization container will permit the entry of sterilizing vapor/gas or other medium to sterilize the contents of the container while denying the ingress of contaminants such as bacteria and other infection causing materials or their vehicles after sterilization. As such, rigid sterilization containers generally provide a consistent barrier against the ingress of contaminants. However, it is difficult to detect if the main seal of typical rigid sterilization containers is properly formed. That is, with the seal gasket integrated within the rigid sterilization container's lid, it is difficult to ascertain that the main seal has properly formed for maintaining the sterility of the container contents post sterilization. Further, it is difficult to detect if the seal gasket is damaged, which could hinder the gasket in the rigid sterilization container from creating an adequate seal against contamination reaching of the contents. Therefore, without opening the rigid sterilization container, one typically does not know if the main seal has maintained its closure or sterility has been maintained from when the rigid sterilization container left the sterilization station to when the contents of the rigid sterilization container are presented for use, e.g., in the OR, where aseptic presentation of the contents is desired.

Consequently, there is a need for a sterilization container that overcomes the shortcomings of known containers. In particular, an indicator for relatively quickly indicating to a user whether a sterilization container is or is not properly sealed, without requiring the user to open the container, would be advantageous. A sterilization container incorporating a visual seal indicator would be desirable. A sterilization container having improved means for closing the container, e.g., to ensure the container is properly sealed, also would be beneficial.

SUMMARY

The present invention provides sterilization containers with features for attaching a lid to a body of the container to seal an interior volume against an ingress of contaminants. The present disclosure also provides visual seal indicators for indicating whether a sterilization container is sealed against an ingress of contaminants. Additional aspects and advantages of the invention will be set forth in part in the following description, may be apparent from the description, or may be learned through practice of the invention.

In one aspect, the present subject matter is directed to a sterilization container that comprises a body, a lid, a gasket, and a seal indicator. The body and lid together define an interior of the sterilization container, and the gasket seals the interior against an ingress of contaminants. The seal indicator is for indicating a seal state of the sterilization container. The seal indicator has a first indicator state that indicates an unsealed container state and a second indicator state that indicates a sealed container state. The seal indicator is in the first indicator state when the gasket is not compressed to seal the sterilization container against the ingress of contaminants, and the seal indicator is in the second indicator state when the gasket is compressed to seal the sterilization container against the ingress of contaminants.

In another aspect, the present subject matter is directed to a method for indicating seal integrity of a gasket of a sterilization container. The method comprises providing a seal indicator for indicating a seal state of the sterilization container. The seal indicator has a first indicium and a second indicium. The method further comprises displaying the first indicium when the sterilization container is in an unsealed state and displaying the second indicium when the sterilization container is in a sealed state. The seal indicator is visible to a user of the sterilization container such that the second indicium is not visible to the user in the unsealed state and the first indicium is not visible to the user in the sealed state.

In still another aspect, the present subject matter is directed to a sterilization container that comprises a body and a lid that together define an interior. The sterilization container further comprises a combination gasket/filter having a gasket for sealing the interior against an ingress of contaminants integrally formed with filter media for forming a barrier between an external environment and the interior. The sterilization container also comprises a seal indicator for indicating a seal state of the sterilization container. The seal indicator has a first indicator state that indicates an unsealed container state and a second indicator state that indicates a sealed container state. The seal indicator is configured to display a first indicium in the first indicator state and is configured to display a second indicium in the second indicator state.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a top, perspective view of a sterilization container according to an exemplary embodiment of the present subject matter.

FIG. 2 provides a side view of the exemplary sterilization container of FIG. 1.

FIG. 3 provides a close-up top, perspective view of a portion of the sterilization container of FIG. 1.

FIG. 4 provides a cross-section view of a portion of the sterilization container of FIG. 1, with the cross-section taken through a seal of the sterilization container, the seal configured as a visual seal indicator as well as a means for sealing the container against an ingress of contaminants.

FIG. 5 provides an end, perspective view of the sterilization container of FIG. 1, with a first seal state of the container indicated by a first visual seal indicator and a second visual seal indicator of the container.

FIG. 6 provides an end, perspective view of the sterilization container of FIG. 1, with a second seal state of the container indicated by a first visual seal indicator and a second visual seal indicator of the container.

FIG. 7 provides an enlarged view of a portion of the sterilization container of FIG. 1, showing a first visual seal indicator and a second seal indicator indicating a second seal state of the container.

FIG. 8 provides a cross-section view of a portion of the sterilization container of FIG. 1, with the cross-section taken through a visual seal indicator assembly and a seal of the sterilization container, the seal configured as a visual seal indicator as well as a means for sealing the container against an ingress of contaminants as described with respect to FIGS. 4-6.

FIGS. 9A and 9B provide a front view and a perspective cross-section view of the visual seal indicator assembly and seal of FIG. 8 in a first seal state of the sterilization container.

FIGS. 10A and 10B provide a front view and a perspective cross-section view of the visual seal indicator assembly and seal of FIG. 8 in a second seal state of the sterilization container.

FIG. 11 provides a side, perspective view of a sterilization container according to an exemplary embodiment of the present subject matter.

FIG. 12 provides an end view of the exemplary sterilization container of FIG. 11.

FIG. 13 provides a schematic cross-section view of the sterilization container of FIG. 11.

FIG. 14 provides a cross-section view of a portion of the sterilization container of FIG. 11, with the cross-section taken through a visual indicator of the sterilization container.

FIG. 15 provides a side, perspective view of a visual indicator assembly for a sterilization container according to an exemplary embodiment of the present subject matter.

FIG. 16A provides a schematic view of a visual indicator assembly for a sterilization container according to an exemplary embodiment of the present subject matter, where the assembly is indicating a first, unsealed state of the sterilization container.

FIG. 16B provides a schematic view of the visual indicator assembly of FIG. 16A, where the assembly is indicating a second, sealed state of the sterilization container.

FIGS. 17, 18, and 19 provide different cross-section views of a portion of the sterilization container of FIG. 11, with the cross-sections taken through a visual indicator of the sterilization container.

FIG. 20 provides a side, perspective view of a sterilization container according to an exemplary embodiment of the present subject matter.

FIG. 21 provides an end view of the exemplary sterilization container of FIG. 20.

FIG. 22 provides a cross-section view of a portion of the sterilization container of FIG. 20, with the cross-section taken through a pump and a visual indicator of the sterilization container.

FIG. 23 provides another cross-section view of a portion of the sterilization container of FIG. 20.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein are a sterilization packaging system or container and components thereof suitable for use in a variety of procedures for containing, sterilizing, storing, and using sterilized items such as surgical devices, instruments, or supplies. While described in conjunction with its use in surgical room procedures located in hospitals or ambulatory surgical facilities, the present subject matter is intended for use wherever there is a need for containerized sterilized devices, instruments, or materials. Consequently, the following description should not be considered a limitation as to the scope of use of the present subject matter.

Generally, the present subject matter provides indicators for indicating the integrity of a seal. For example, described herein are seal indicators of sterilization containers that indicate whether the sterilization container is sufficiently sealed to prevent an ingress of contaminants into the sterilization container. If the sterilization container is sufficiently sealed, the seal indicator is in one state, and if the sterilization container is not sufficiently sealed, the seal indicator is in another state. Thus, the state of the sterilization container is communicated to a user through visible indicia of the seal indicator. That is, the seal indicator undergoes a visible change in state when the sterilization container transitions from not being sealed, e.g., when articles are being placed in the container for sterilization, to being sealed, e.g., when a lid of the container is properly secured to a body of the container, such that the user may be assured that the container is properly sealed to maintain sterility of the articles therein post-sterilization. Further, the seal indicator undergoes a visible change in state if the seal is broken after the lid is secured to the container, to signal to the user that the seal has been breached such that the articles in the container may no longer be sterile. However, the seal indicator does not undergo a state change when the container is subjected to a sterilization process or protocol, i.e., the state change associated with the closure or sealing of sealing of the container is unaffected by the sterilization modality. The sterilization process or modality includes delivery of a sterilization agent such as steam, ethylene oxide, hydrogen peroxide plasma, etc. to an interior of the container to sterilization the container's contents. The present subject matter also provides methods for indicating a seal state of a sterilization container.

Referring particularly to FIGS. 1 through 4, FIG. 1 provides a top, perspective view of a sterilization container 10 according to an exemplary embodiment of the present subject matter. FIG. 2 provides a side view of the exemplary sterilization container 10, and FIG. 3 provides a close-up top, perspective view of a portion of the sterilization container 10. FIG. 4 provides a schematic cross-section view of a portion of the sterilization container 10, with the cross-section taken through a gasket of the sterilization container 10 that is configured as both a visual seal indicator 20 and a means for sealing the container against an ingress of contaminants.

As shown in FIGS. 1 and 2, the sterilization container 10 comprises a body 12 and a cover or lid 14. The lid 14 is retained on the body 12 by one or more latches 16, e.g., each latch 16 includes a pivotable element that engages a catch, where the pivotable element may be attached to either the body 12 or the lid 14 and the catch is formed on the other of the body 12 or lid 14. Further, the container 10 includes one or more handles 18 for lifting, carrying, or otherwise handling the container 10. For example, as illustrated in FIGS. 1 and 2, a first handle 18a may be attached to a first end 12a of the body 12, and a second handle 18b may be attached to a second end 12b of the body 12, where the second end 12b is opposite the first end 12a. In other embodiments, the first handle 18a may be attached to a first side 12c of the body 12, and the second handle 18b may be attached to a second side 12d of the body 12, where the second side 12d is opposite the first side 12c and the first and second sides 12c, 12d extend between the first and second ends 12a, 12b. Other configurations and/or placements of one or more handles 18 may be used as well. Additionally, it will be appreciated that the sterilization container 10 may generally have the form of a parallelepipedal box shape as shown in FIG. 1, and the container 10 may have any appropriate size for containing items to be sterilized.

As further depicted in FIGS. 1-4, a visual seal indicator 20 provides a visual indication of a seal state of the sterilization container 10. For instance, the seal indicator 20 indicates to a user of the container 10 whether the container 10 is in a first, unsealed state, where the container 10 is not sealed against an ingress of contaminants (i.e., contaminants could enter the container 10), or a second, sealed state, where the container 10 is sealed against the ingress of contaminants (i.e., contaminants cannot enter the container 10). That is, the seal indicator 20 is a binary indicator of the integrity of the seal between the body 12 and lid 14 of the container 10, e.g., the indicator 20 indicates when the seal is established and when the seal is broken or otherwise compromised and is unaffected by the sterilization modality to which the container 10 is subjected to sterilize the articles within the container. More particularly, the seal indicator 20 has a first indicator state that indicates the unsealed container state and a second indicator state that indicates the sealed container state. The seal indicator 20 is visible to a user of the container 10 from an exterior 22 of the container 10 to signal to the user whether the container is sealed or unsealed. A change in state, i.e., from the first indicator state to the second indicator state or from the second indicator state to the first indicator state, may be achieved by a change in color, shape, size, position, etc. of the seal indicator 20 to signal the container 10 has transitioned from its unsealed state to its sealed state or from its sealed state to its unsealed state. Various embodiments of seal indicators, such as seal indicator 20, are described in greater detail herein.

The seal between the body 12 and the lid 14 is established by a gasket 24. The gasket 24 seals an interior 26 of the container 10, which is defined by the body 12 and lid 14 together, against the ingress of contaminants. That is, the gasket 24 extends between the body 12 and lid 14. For instance, the gasket extends about a perimeter of an open top portion 28 of the body 12 and an interface portion 30 of the lid 14. Securing the lid 14 to the body 12 compresses the gasket 24 between the body 12 and lid 14 to seal the interior 26. When the gasket 24 is not compressed, or not fully compressed, such that the interior 26 is not sealed against the ingress of contaminants, the container 10 is in its first, unsealed state and the seal indicator 20 is in its first indicator state. Similarly, when the gasket 24 is fully compressed, such that the interior 26 is sealed against the ingress of contaminants, the container 10 is in its second, sealed state and the seal indicator 20 is in its second indicator state.

As described in greater detail herein, in some embodiments of seal indicators, such as seal indicator 20, the seal indicator is configured to display a first indicium in the first indicator state and is configured to display a second indicium in the second indicator state. The first indicium may be a first color or hue and the second indicium may be a second color or hue, and the first and second colors or hues may be selected such that there is a high contrast between the colors/hues and/or between the colors/hues and the sterilization container 10, and/or the colors/hues may be selected to reinforce the signal communicated by the color or hue. For example, in an exemplary embodiment, the first color is red to indicate the container 10 is unsealed (i.e., contaminants could enter the container 10 and reach any articles in the interior 26), and the second color is green to indicate the container 10 is sealed (i.e., contaminants cannot enter the container 10 and any articles in the container 10 would remain sterile after sterilization). Thus, the seal indicator 20 is configured to display the first color when the container 10 is unsealed and the second color when the container 10 is sealed, such that the seal indicator 20 indicates a change in the seal state of the container 10 through a change in color.

As shown in the figures, in some embodiments, the seal indicator 20 is visible from the exterior 22 of the container 10 through an opening, such as a window or the like, in the body 12. In other embodiments, the seal indicator 20 is visible from the exterior 22 of the container 10 through an opening, such as a window or the like, in the lid 14. In exemplary embodiments, a plurality of openings are defined in the body 12 and/or lid 14 such that the seal indicator 20 is visible from each of the first end 12a, the second end 12b, the first side 12c, and the second side 12d of the body 12.

Referring to FIGS. 1 and 2, a plurality of openings 32 are defined in the lid 14 about the perimeter of the lid 14. Further, the gasket 24 is the seal indicator 20, i.e., one component, the gasket 24, both seals the container 10 and indicates to a user whether the container 10 is sealed against the ingress of contaminants, thus performing both the sealing and indicating functions. For example, the gasket 24 comprises a first indicium 20a to indicate the first indicator state and a second indicium 20b to indicate the second indicator state. More particularly, the gasket 24 shown in FIG. 1 is made from a deformable material molded in two different colors, as described in greater detail herein. The container 10 may further include a second indicator 42, which may also be an indicator of seal integrity. In other embodiments, the second indicator 42 may indicate whether the container 10 has undergone sterilization. As such, the gasket 24 and the second indicator 42 together indicate whether the contents of the container 10 have been and remain sterilized.

As illustrated most clearly in FIGS. 3 and 4, the seal indicator 20 or gasket 24 is visible through the plurality of openings 32 defined the lid 14 of the container 10. The first indicium 20a is visible through the openings 32 when the container 10 is in its first, unsealed state, and the second indicium 20b is visible through the openings 32 when the container 10 is in its second, sealed state. Thus, the seal indicator alternates between displaying the first indicium 20a and the second indicium 20b, i.e., the same indicium (first indicium 20a or second indicium 20b) is visible in all of the openings 32 at the same time.

As shown in FIG. 4, the container body 12 has a top lip 34 around its perimeter, and the lid 14 defines a groove 36 around its perimeter. The gasket 24 extends in the groove 36 between the top lip 34 of the body 12 and an inner groove surface 38 of the lid 14. The gasket 24 may be a double channeled gasket as illustrated in FIG. 4. More particularly, the gasket 24 shown in the exemplary embodiment comprises a first gasket portion 24a and a second gasket portion 24b. It will be appreciated that the gasket 24 extends fully around the perimeter of the body 12 and the perimeter of the lid 14 and that the gasket 24 provides an air tight seal. Thus, the gasket 24 seals the interior 26 of the sterilization container 10 against the ingress of contaminants.

In the embodiment illustrated in FIGS. 1-4, each opening 32 of the plurality of openings 32 is a shaped orifice, such as a slit, i.e., a long narrow opening, in the lid 14. It will be appreciated that the openings 32 may have other shapes than as shown in the figures, e.g., each opening 32 may be circular, oval, rectangular, etc. As previously described, the first indicium 20a is visible through the openings 32 when the sterilization container 10 is in its unsealed state, and the second indicium 20b is visible through the openings 32 when the sterilization container 10 is in its sealed state. Accordingly, at a given moment, each opening 32 displays the same indicium therethrough, i.e., the first indicium 20a will not be visible through a first opening 32 while the second indicium 20b is visible through a second opening 32. Rather, either the first indicium 20a or the second indicium 20b will be visible through both the first and second openings 32 (as well as any other openings 32 through which the gasket 24 is visible). Therefore, the first and second indicia 20a, 20b are alternately visible through the openings 32, and different openings 32 do not display different indicia 20a, 20b but all openings 32 display the same indicia 20a, 20b.

To relatively quickly communicate to the user the seal state of the container 10, the gasket 24 may be dual colored such that a first color of the dual colored gasket 24 is the first indicium 20a and a second color of the dual colored gasket 24 is the second indicium 20b. In an exemplary embodiment, the gasket 24 is made from a deformable material that is molded in two different colors or hues such that a first color or hue of the two different colors or hues is the first indicium 20a and a second color or hue of the two different colors or hues is the second indicium 20b. The first and second colors/hues may be contrasting or complementary colors, i.e., colors that are directly opposite each other in the color spectrum or on the color wheel, e.g., to enable clear differentiation between the first indicium 20a and the second indicium 20b. For example, the first color may be red and the second color may be green. The deformable material forming the gasket 24 extends around a perimeter of the container body 12, e.g., around the top lip 34, and the deformable material gasket 24 is in contact with the body 12 and container lid 14 when the lid 14 is positioned on the body 12. The gasket 24 formed from the deformable material displays the first indicium 20a to the user when the deformable material is not compressed or is not sufficiently compressed to seal the sterilization container 10, i.e., when contaminants could enter the container 10 and the container 10 is, thus, unsealed. The gasket 24 displays the second indicium 20b to the user when the deformable material is sufficiently compressed to seal the sterilization container 10, i.e., when contaminants cannot enter the container 10 and the container 10 is, thus, sealed. Therefore, as shown in FIGS. 5 and 6 illustrating an exemplary embodiment of a dual colored gasket 24, the first color (e.g., red) is visible through the openings 32 when the gasket 24 is not compressed to an extent to prevent contaminants from entering the interior 26 of the container 10 (FIG. 5), and the second color (e.g., green) is visible through the openings 32 when the gasket 24 is compressed to a sufficient extent to prevent contaminants from entering the interior 26 (FIG. 6). As previously stated, the gasket 24 extends within a groove 36 defined in the lid 14, and the first and second indicia 20a, 20b are displayed through openings 32 defined in the lid 14. The openings 32 may be defined along the entire perimeter of the lid 14, e.g., as shown in FIG. 1, such that the seal indicator 20 is visible from any side of the container 10, e.g., from the first and second ends 12a, 12b and first and second sides 12c, 12d of the body 12. In other embodiments, the openings 32 may be formed at certain locations along the lid perimeter, such that the seal indicator 20 is visible from only certain sides of the container 10.

As depicted in FIGS. 2, 7, and 8, the sterilization container 10 also may comprise a second indicator assembly 40, which includes a second visual seal indicator 42 visible through a window 44 in the container lid 14. In some embodiments, when used in conjunction with the gasket 24 having first and second indicia 20a, 20b, the second indicator 42 is a secondary indicator of the integrity of the seal between the body 12 and lid 14 and, thereby, whether sterility of the contents of the container 10 has been maintained if the container 10 has undergone a sterilization protocol. That is, where the sterilization container 10 includes both a gasket 24 having visible first and second indicia 20a, 20b and a second indicator assembly 40 having a second seal indicator 42, one of the gasket 24 and the second seal indicator 42 may be referred to as a primary seal indicator and the other of the gasket 24 and second seal indicator 42 may be referred to as a secondary seal indicator. In other embodiments, the second seal indicator 42 may be the only indicator of seal integrity provided with the container 10, i.e., the container 10 includes the second seal indicator assembly 40 but not the gasket 24 having visible first and second indicia 20a, 20b.

Likewise, in some embodiments, the seal indicator 20, i.e., the gasket 24, may be the only visual seal indicator for the container 10. That is, the container 10 does not include a second indicator of seal integrity, but as previously stated, the second indicator assembly 40 may indicate whether the sterilization container 10 has undergone a sterilization protocol (rather than indicate whether the integrity of the seal between the body 12 and lid 14 has been established and maintained) and, thus, may be a sterility indicator. For example, the second indicator assembly 40 may include an indicator visible through a window 44 in the container lid 14 that changes from a first state to a second state upon exposure to sufficient sterilization conditions to sterilize the contents of the container 10. As one example, the second indicator 42 of the second indicator assembly 40 may be configured to transition from the first state to the second state upon exposure to steam at a certain temperature for a certain amount of time. Thus, the second indicator assembly 40 may be a sterility indicator instead of a seal integrity indicator, and when used in conjunction with the indicator gasket 24, the indicators 20, 40 of the container 10 may indicate whether a seal has been established and maintained through a sterilization protocol such that the contents of the container 10 are sterile. In other embodiments, the second indicator assembly 40 may be omitted altogether, i.e., the seal indicator 20 may be the only indicator of seal integrity and no indication of whether the container 10 has undergone a sterilization process may be provided.

Like the gasket 24 described with respect to FIGS. 1-4, in embodiments in which the second indicator 42 is a seal integrity indicator, the second seal indicator 42 includes a first indicium 46 and a second indicium 48. The second seal indicator 42 also may be referred to as an indicator segment that includes the first indicium 46 to indicate a first indicator state and the second indicium 48 to indicate a second indicator state. The first indicator state, in turn, indicates to a user that the sterilization container 10 is in its first, unsealed state, and the second indicator state indicates to the user that the container 10 is in its second, sealed state. Further, the first indicium 46 and the second indicium 48 of the second seal indicator 42 are alternately visible through the window 44, which in the depicted exemplary embodiment is defined in the container lid 14. That is, the first indicium 46 is visible when the container 10 is in the unsealed state, and the second indicium 48 is visible when the container 10 is in the sealed state. The second indicator assembly 40 alternates between displaying the first indicium 46 and the second indicium 48 depending on the seal state of the container 10. Further, as described with respect to seal indicator 20, the second indicator assembly 40 is unaffected by the sterilization modality to which the container 10 is subjected to sterilize the articles within the container 10 such that the second indicator assembly 40 transitions between the first indicium 46 and second indicium 48 only in response to a change in seal state of the container 10.

Referring now to FIGS. 8, 9A, 9B, 10A, and 10B, the second seal indicator assembly 40 will be described in greater detail. As shown in FIGS. 8, 9B, and 10B, the second seal indicator assembly 40 comprises a plunger 50 extending between the gasket 24 and the second seal indicator 42, which includes the first indicium 46 and the second indicium 48. The second seal indicator assembly 40 further comprises a platform 52 at a distal end 60 of the assembly 44. When the gasket 24 is compressed to seal the container interior 26 against the ingress of contaminants, the gasket 24 contacts the platform 52, and the platform 52 is in operative communication with the plunger 50 such that the plunger 50 is displaced when the gasket 24 contacts the platform 52. More particularly, the second seal indicator 42 is positioned on or against one end of the plunger 50 such that the plunger 50 and second seal indicator 42 are in operative communication. Further, the platform 52 is positioned on or against the end of the plunger 50 opposite the second seal indicator 42 such that the platform 52 and plunger 50 are in operative communication. When the plunger 50 is displaced, it in turn displaces the second seal indicator 42, which causes the second seal indicator 42 to transition from displaying the first indicium 46 to displaying the second indicium 48. Accordingly, when the container 10 transitions from the first, unsealed state, where the gasket 24 is not compressed or not sufficiently to seal the interior 26, to the second, sealed state, where the gasket 24 is sufficiently compressed to seal the interior 26, the second seal indicator 42 transitions from displaying the first indicium 46 in the window 44 to displaying the second indicium 48 in the window 44. As shown, the second seal indicator 42 is at a proximal end 54 of the plunger 50, i.e., opposite the platform 52 that is at a distal end 56 of the plunger 50.

As illustrated in the figures, the second indicator assembly 40 also may include a biasing member 58 that helps position the second seal indicator 42 adjacent the window 44. More specifically, the biasing member 58, which may be a spring or the like, helps locate the correct indicia 46, 48 in the window 44 for the current seal state of the container 10 such that the second indicator assembly 40 correctly indicates the current seal state to the user of the container 10. In some embodiments, the biasing member 58 may be biased to default to a position in which a certain seal state is indicated in the window 44. For example, the biasing member 58 may default to a position in which the first indicium 46, indicating the first, unsealed state of the sterilization container 10, is displayed in the window 44.

The biasing member 58 extends between a stop and the second seal indicator 42. In some embodiments, the second seal indicator 42 and the biasing member 58 are disposed within a housing 60 such that the stop is a portion of the housing 60. For instance, as illustrated in FIG. 8, the stop is an upper wall 62 of the housing 60, and the biasing member 58 is positioned between the upper wall 62 and the second seal indicator 42. As another example, illustrated in FIGS. 9B and 10B, the stop is a lower wall 64 of the housing 60, and the biasing member 58 is positioned between the second seal indicator 42 and the lower wall 64.

Referring to FIGS. 9A, 9B, 10A, and 10B, in an exemplary embodiment, the second seal indicator 42 of the second seal indicator assembly 40 is dual colored. A first color of the dual colored second seal indicator 42 is the first indicium 46, and a second color of the dual colored second seal indicator 42 is the second indicium 48. In FIGS. 9A and 9B, the second seal indicator assembly 40 is displaying the first color, which is red in the exemplary embodiment. As described, the first color is the first indicium 46, which indicates an incomplete or unsealed seal state of the container 10. In FIGS. 10A and 10B, the second indicator assembly 40 is displaying the second color, which is green in the exemplary embodiment. As described, the second color is the second indicium 48, which indicates a complete or sealed seal state of the container 10. As previously described, in the unsealed state, the gasket 24 of the sterilization container 10 is not sufficiently compressed to seal the container 10 against the ingress of contaminants. In the sealed state, the gasket 24 is sufficiently compressed to seal the container 10 against the ingress of contaminants, and the compression of the gasket 24 displaces the plunger 50, e.g., by the gasket 24 pressing on the platform 52, which in turn displaces the second seal indicator 42 to transition from displaying the first indicium 46 (e.g., the first color, which may be red) to displaying the second indicium 48 (e.g., the second color, which may be green). Thus, the second indicator assembly 40 alternates between displaying the first indicium 46 and the second indicium 48 depending on the seal state of the container 10, such that the first and second indicia 46, 48 are alternately visible through the window 44.

Referring back to FIGS. 5 and 6, in some embodiments, the sterilization container 10 incorporates both the visual seal indicator 20 and the second indicator assembly 40. As such, when the container 10 is unsealed or in the first seal state, each visual seal indicator 20, 40 displays its respective first indicium 20a, 46. Likewise, when the container 10 is sealed or in the second seal state, each visual seal indicator 20, 40 displays its respective second indicium 20b, 48. In this way, a user of the container 10 may easily be able to determine whether the container 10 is properly sealed against the ingress of contaminants. Further, if the container 10 has undergone a sterilization procedure, the user may be able to easily determine whether contents of the container 10 are sterile (i.e., the container 10 is in its second, sealed state) or their sterility has been compromised (i.e., the container 10 is in its first, unsealed state).

In other embodiments, the visual seal indicator 20 and/or the second visual seal indicator 42 may comprise other features for indicating the seal state of the container 10. As an example, rather than being dual colored, the gasket 24 may have two different visual patterns thereon, and a first pattern may be displayed when the container 10 is in the unsealed state, and a second pattern may be displayed when the container 10 is in the sealed state. As another example, rather than being dual colored, the second seal indicator 42 may have two different images printed thereon; a first image may be displayed when the container 10 is in the unsealed state, and a second image may be displayed when the container 10 is in the sealed state. Other visual indicia, e.g., color differences, words, etc., and other types of indicators 20, 40, such as auditory or other non-visual indicators, may be used as well. Further, the indicators 20, 40 may utilize other state changes, such as a transition from a first position to a second position or a transition from a first shape to a second shape, to indicate whether the integrity of the seal between the container body 12 and lid 14 remains intact or has been compromised. That is, the seal indicators 20, 40 may use a change in state, such as a change in color, position, or shape, to indicate the seal state of the container 10, which indicates seal integrity to a user of the container 10.

Moreover, in some embodiments, the sterilization container 10 may include a system that compensates for a loss of pressure over time. For example, the gasket 24 may be configured to maintain its seal over a certain change in pressure (e.g., a given percentage decrease in the seal's internal pressure), and in some embodiments, the container 10 may have one or more features that enable its gasket 24 to maintain its effectiveness over time. Such feature(s) may compensate for pressure loss over an indefinite period of time. In other embodiments, the container 10 may be understood to have a limited shelf life, e.g., such a pressure compensation system may be omitted or may be effective only for a finite period of time. In such embodiments, the sterilization container 10 may be marked, sorted, or the like such that a user can ascertain how much longer the contents of a given container 10 should remain sterile.

Additionally, the sterilization container 10 may be balanced such that small pressure changes that would otherwise occur (i.e., in an unbalanced system) may be reduced or eliminated. For instance, balancing may reduce or eliminate the heat or steam impacts on the sterilization container 10 and its gasket 24 as the container 10 undergoes a sterilization process. Further, each visual seal indicator 20, 40 may be sealed or otherwise protected against impacts from the heat, steam, and/or chemical sterilant used in the sterilization process, e.g., to preserve the integrity of the seal indicator 20, 40 such that it continues to indicate the proper seal state of the container 10. In still further embodiments, the sterilization container 10 may include tamper evidence to alert a user that the container 10 has been tampered with or has been used and/or tamper prevention to prevent tampering with the container 10.

Accordingly, as described with respect to FIGS. 1-10B, the present subject matter provides sterilization containers with features for sealing against an ingress of contaminants such that each container remains sealed during and after undergoing a sterilization process or protocol, as well as features for indicating a seal state of the container. For instance, the container may include a gasket or seal that, in addition to sealing the container against contamination, is a visual seal indicator that visually indicates the seal state of the container through a window, e.g., defined in a body or lid of the container. For example, the visual seal indicator may be a binary indicator that displays either a first indicium or a second indicium through the window. The first indicium may indicate a first, unsealed state of the container, e.g., state where contaminants could enter an interior of the container. The second indicium may indicate a second, sealed state of the container, e.g., where contaminants cannot enter the interior of the container. The first and second indicia may be a first color and a second color, a first image and a second image, a first pattern and a second pattern, etc. As another example, the visual seal indicator may be separate from the container seal and may, for example, be part of an assembly that comprises a plunger that displaces the visual seal indicator when the container is sealed to transition from displaying the first indicium to displaying the second indicium in a window defined in the container, e.g., in the container body or lid. The sterilization containers and visual seal indicators described herein provide containers for sterilizing items, such as medical instruments or the like, that may be sealed against an ingress of contaminants, may retain their seal, and may easily communicate to a user of the container whether the container is or is not properly sealed. Other advantages of the present subject matter also may be apparent to one of ordinary skill in the art.

Turning now to FIGS. 11 through 23, additional embodiments of the present subject matter will be described. FIG. 11 provides a side, perspective view of a sterilization container 100 according to an exemplary embodiment of the present subject matter. FIG. 12 provides an end view of the exemplary sterilization container 100. As shown in FIGS. 11 and 12, the sterilization container 100 comprises a body 102 and a cover or lid 104. The lid 104 is retained on the body 102 by one or more latches 106, e.g., a pivotable element that engages a catch, where the pivotable element may be attached to either the body 102 or the lid 104 and the catch is formed on the other of the body 102 or lid 104. Further, the container 100 includes one or more handles 108 for lifting, carrying, or otherwise handling the container 100. For example, a first handle 108 may be attached to a first end 102a of the body 102, as illustrated in FIGS. 11 and 12, and a second handle 108 may be attached to a second end 102b of the body 102, where the second end 102b is opposite the first end 102a. In other embodiments, a first handle 108 may be attached to a first side 102c of the body 102, and a second handle 108 may be attached to a second side 102d of the body 102, where the second side 102d is opposite the first side 102c and the first and second sides 102c, 102d extend between the first and second ends 102a, 102b. Other configurations and/or placements of one or more handles 108 may be used as well. Additionally, it will be appreciated that the sterilization container 100 may generally have the form of a parallelepipedal box shape as shown in FIG. 11, and the container 300 may have any appropriate size for containing the article(s) to be sterilized.

As further depicted in FIGS. 11 and 12, a visual seal indicator 110 provides a visual indication of a seal state of the sterilization container 100. For instance, the seal indicator 110 has a first indicator state and a second indicator state. In the first indicator state, the indicator 110 indicates to a user of the container 100 that the container 100 is in a first seal state, where the container 100 is not sealed against an ingress of contaminants (i.e., contaminants could enter the container 100). In the second indicator state, the indicator 110 indicates to the user that the container 100 is in a second seal state, where the container 100 is sealed against the ingress of contaminants (i.e., contaminants cannot enter the container 100). The first seal state also may be referred to as the unsealed state of the container 100, and the second seal state also may be referred to as the sealed state of the container 100. As such, the seal indicator 110 is a binary indicator of a change in pressure of a seal 120 of the container 100, e.g., the indicator 110 indicates when the seal is established and when the seal is broken or otherwise changes in pressure. The seal indicator 110 is described in greater detail herein.

Turning to FIG. 13, a schematic cross-section view is provided of the sterilization container 100. As shown in FIG. 13, the container body 102 has a top lip 112 around its perimeter, and the lid 104 defines a groove 114 around its perimeter. The groove 114 has an inner groove surface 116. The top lip 112 defines a bottom sealing surface 118 and the inner groove surface 116 forms a top sealing surface. A seal 120 that includes a gasket 122 and a space 124 extends from the bottom sealing surface 118 to the top sealing surface, or inner groove surface, 116. As illustrated in FIG. 13, the gasket 122 may be a double gasket. More particularly, the gasket 122 shown in the exemplary embodiment comprises a first gasket portion 122a and a second gasket portion 122b. The space 124 is defined between the first gasket portion 122a and the second gasket portion 122b. Alternatively, the gasket 122 may be a channeled gasket, with the space 124 defined within the channel of the gasket 122. In either embodiment, the space 124 is enclosed by the gasket 122, the bottom sealing surface 118, and the top sealing surface 116. Moreover, the gasket 122 extends within the groove 114 in contact with the top lip 112 and the inner groove surface 116, as well as the side walls 115 of the groove, which help support the gasket 122. Further, it will be appreciated that the seal 120 extends fully around the perimeter of the body 102 and the perimeter of the lid 104 and that the seal 120 is an air tight seal.

A vacuum is pulled within the space 124 to seal the sterilization container 100 against an ingress of contaminants. For example, the vacuum may be pulled when the sterilization container 100 undergoes a sterilization process, i.e., the temperature and/or pressure to which the container 100 is subjected during sterilization creates a vacuum within the space 124, which seals an interior or sterile space 126 of the container 100 such that contaminants cannot enter the interior 116.

Referring now to FIGS. 14 through 19, the seal indicator 110 will be described in greater detail. FIG. 14 provides a cross-section view of a portion of the sterilization container 100, with the cross-section taken through the seal indicator 110. As previously stated, the indicator 110 indicates a seal state of the sterilization container 100, such as a first seal state in which the container 100 is not sealed against contaminants (i.e., contaminants could enter the container 100) and a second seal state in which the container 100 is sealed against contaminants (i.e., contaminants cannot enter the container 100). In the depicted exemplary embodiment, the container body 102 defines a window 128 for a user to view the seal indicator 110. That is, in the illustrated embodiment, the seal indicator 110 is internal to the sterilization container 100, and the seal state indicated by the seal indicator 110 is visible through the window 128 in the container body 102. Alternatively, the window 128 may be defined in the lid 104 rather than the body 102 of the container 100 such that the seal indicator 110 is visible through the window 128 in the lid 104. More than one window 128 may be defined in the container 100, e.g., such that the indicator 100 is visible from one or more sides of the container 100.

In the exemplary embodiment shown in FIGS. 14-19, the seal indicator 110 comprises a visual indicator assembly 130 for actuating the seal indicator 110 between the first seal state and the second seal state. Referring particularly to FIG. 15, the visual indicator assembly 130 comprises a stem 132 and at least one bimetal washer 134. The stem 132 is positioned to contact the seal indicator 110, and the at least one bimetal washer 134 contacts the stem 132 such that the at least one bimetal washer 134 displaces the stem 134 when the washer 134 expands, bends, or otherwise deforms (e.g., changes shape or size) upon heating, e.g., being heated above a threshold temperature. It will be appreciated that a sufficient number of bimetal washers 134 are provided to displace the stem 134 a needed length or distance. The visual indicator assembly 130 may include three bimetal washers 134 or six bimetal washers 134 as shown in the illustrated embodiments, but it will be understood that in other embodiments, one, two, or more than three washers 134 may be used.

The visual indicator assembly 130 also may include a biasing member 136, such as a spring or the like, to help hold an indicator strip or segment 138 in position with respect to the window 128. More particularly, as illustrated in FIG. 16A, the stem 132 is positioned to contact the indicator segment 138, and the biasing member 136 may bias the stem 132 to a certain position such that the indicator segment 138 defaults to a position in which the first, unsealed state is indicated to a user of the sterilization container 100. Upon sterilization, where the sterilization container 100 is heated to sterilize its contents, the one or more bimetal washers 134 expand or deform as shown in FIG. 16B, and the stem 132 is displaced to a position such that the indicator segment 138 indicates to the user that the container 100 is in its second seal state (i.e., sealed). For instance, the stem 132 may displace the indicator segment 138 relative to the window 128 to change what seal state is indicated or displayed to the user. As illustrated in FIGS. 16A and 16B, the biasing member 136 may be positioned between a distal end 144 of the stem 132 and the bimetal washer(s) 134, where the distal end 144 defines a stop against which the biasing member 136 may act.

In some embodiments, the seal indicator 110 comprises a dual colored indicator segment 138. A first color 138a of the dual colored indicator segment 138 indicates the first seal state and a second color 138b of the dual colored indicator segment 138 indicates the second seal state. More particularly, when the sterilization container 100 is not sealed against the ingress of contaminants, the seal indicator 110 displays the first color 138a in the window 128. That is, only a portion of the indicator segment 138 is visible in the window 128 such that a single color may be displayed in the window 128. Likewise, when the sterilization container 100 is sealed against the ingress of contaminants, the seal indicator 110 displays the second color 138b in the window 128. Accordingly, by viewing the indicator segment 138, a user can relatively quickly ascertain whether the sterilization container 100 is sterile or not sterile, or more specifically, the user can determine whether the contents of the container 100 are or are not sterile.

Referring to FIGS. 16A and 16B, one example of an indicator 110 having a dual colored indicator segment 138 is provided. As shown in FIG. 16A, before sterilization or when the sterilization container 100 has not been exposed to sufficient heat to cause the bimetal washers 134 to expand or deform, the indicator segment 138 displays a second color 138b, such as red, in the window 128. Once the container 100 is exposed to sufficient heat, the bimetal washers 134 expand or deform as illustrated in FIG. 16B, displacing the stem 132 and thereby displacing the indicator segment 138 such that a second color 138b, such as green, is displayed in the window 128. Thus, when a user sees the first color 138a (e.g., red) in the window 128, the user can determine that the contents of the sterilization container 100 are not sterile, but when the user sees the second color 138b (e.g., green) in the window 128, the user can determine the container contents are sterile.

As further illustrated in FIG. 16B, the bimetal washers 134 are arranged such that the washers 134 alternate in a direction of deformation. That is, a first washer 134a deforms into a convex shape relative to a vertical direction V, a second washer 134b adjacent the first washer 134a deforms into a concave shape relative to the vertical direction, a third washer 134c adjacent the second washer 134b deforms into a convex shape relative to the vertical direction, and so on with respect to the fourth, fifth, and sixth washers 134d, 134e, 134f. As such, the first, third, and fifth washers 134a, 134c, 134e are all a convex shape upon deformation while the second, fourth, and sixth washers 134b, 134d, 134f are all a concave shape upon deformation. Alternating the direction of deformation between the washers 134 helps displace the stem 132, e.g., by the washers 134 pushing against the biasing member 136, which in turn pushes against the stop at the distal end 144, and the indicator segment 138.

In other embodiments, the seal indicator 110 may comprise other features for indicating the seal state of the container 100. As an example, rather than being dual colored, the indicator segment 138 may have two different visual patterns thereon, and a first pattern may be displayed when the container 100 is in the first seal state (i.e., unsealed), and a second pattern may be displayed when the container 100 is in the second seal state (i.e., sealed). Other visual indicia, e.g., images, color differences, words, etc., and other types of indicators 110, such as auditory or other non-visual indicators, may be used as well.

Further, in some embodiments, the two colors of the dual colored indicator segment 138 may be reversed with respect to the order of the colors shown in the figures. That is, the first color 138a (e.g., red) that indicates the first seal state (i.e., unsealed) may be on the bottom of the indicator segment 138 while the second color 138b (e.g., green) that indicates the second seal state (i.e., sealed) may be on top. It will be appreciated that, in different embodiments, the visual indicator assembly 130 may act in different directions. For instance, in the depicted embodiment, the stem 132 retracts upward such that the indicator segment 138 is pulled upward by the stem 132 to display the second color 138b in the window 128, but in other embodiments, the stem 132 may be displaced downward such that the indicator segment 138 is pushed downward by the stem 132 to display the second color 138b in the window 128. Of course, the visual indicator assembly 130 may have other configurations as well.

As illustrated in FIGS. 17-19, the visual indicator assembly 130 also may have other features. For example, the at least one bimetal washer 134 is disposed within a housing 140, and a pad 142 at a distal end 144 of the stem 132 may contact the top lip 112 of the container body 102 when the seal indicator 110 is assembled with the sterilization container 100. More specifically, as shown in FIGS. 17, 18, and 19, the top lip 112 defines a recess 146 in which the stem distal end 144, the pad 142, the housing 140, and the one or more washers 134 are disposed. As the washer(s) 134 expand or deform and displace the stem 132, the pad 142 presses against an underside 148 of the top lip 112 within the recess 146, which may help displace the stem 132 to display the indicator of the second seal state (such as the second color 138b, e.g., green, of a dual colored indicator segment 138) in the window 128 defined in the body 102. As depicted in FIG. 19, in some embodiments, a plurality of apertures 150 may be defined in the top lip 112 adjacent the pad 142, allowing fluid communication between the cavity 152 in which the seal 120 is disposed and the recess 146. When the bimetal washer(s) 134 expand or deform and displace the stem 132, the pad 142 contacts the lip underside 148 at the apertures 150 such that the recess 146 is no longer in fluid communication with the cavity 152. As such, the pad 142 may help enclose the seal space 124 such that a vacuum may be established in the space 124 to adequately seal the sterilization container 100 against the ingress of contaminants. The visual indicator assembly 130 and/or the sterilization container 100 also may include features for maintaining the closure of the apertures 150 after the container 100 is no longer being heated to sterilize its contents (which causes the bimetal washer(s) 134 to contract, flatten, or otherwise return to a first or baseline state or configuration) such that the vacuum may be maintained in the space 124 to ensure the container 100 remains sealed.

Further, the visual indicator assembly 130 may include at least a portion of a fastener 154 for latching or securing the lid 104 to the body 102. For example, the assembly 130 may include a female portion 154a of the fastener 154 and the lid 104 may include a male portion 154b of the fastener 154. In the depicted embodiment, the pivotable element of a latch 106 attached to the lid 104 includes the male portion 154b, such that the fastener 154 may be fastened or unfastened by manipulating the latch 106. That is, when the pivotable element of the latch 106 is raised or unfastened, the male portion 154b is removed from the female portion 154a to unlatch or unsecure the lid 104 with respect to the container body 102. Of course, the fastener 154 and/or its constituent parts may be separate from the visual indicator assembly 130 and need not be co-located with the assembly 130 as shown in the depicted embodiment.

Moreover, unlike the embodiment shown in FIGS. 16A and 16B, the biasing member 136 may be located on the stem 132 between the housing 140 and a stop 156, as shown in FIGS. 15 and 17. As previously described, the biasing member 136 may deform to urge the stem 132 to a desired position when the bimetal washer(s) 134 deform. The biasing member 136 may act against the housing 140 and stop 156 to bias the stem 132 to a particular position.

Additionally, although described herein as activated by heat, it will be appreciated that, in other embodiments, the assembly 130 may be activated by other mechanisms or processes. For instance, the assembly 130 may be pressure activated or activated by chemical exposure, e.g., the bimetal washer(s) 134 may deform when subjected to a pressure above a threshold pressure. The assembly 130 may be configured to be activated by any suitable feature of a sterilization protocol, e.g., temperature, pressure, exposure to certain chemicals or combinations of chemicals, etc. That is, the assembly 130 may be configured to respond to one or more features or processes of the sterilization protocol to display the appropriate indicator to a user of the sterilization container 100.

Turning now to FIGS. 20 through 23, a sterilization container according to another exemplary embodiment of the present subject matter will be described. For this embodiment, the seal is manually activated rather than activated upon exposure to a particular temperature, pressure, or other condition, e.g., during a sterilization protocol. As shown in FIGS. 20-23, the depicted embodiment utilizes a manual pump to pressurize a seal or gasket and thereby seal a sterilization container against an ingress of contaminants. More particularly, FIG. 20 provides a side, perspective view and FIG. 21 provides an end view of an exemplary sterilization container 200. As shown in FIGS. 20 and 21, the sterilization container 200 is similar to the sterilization container 100 described above, comprising a body 202 and a cover or lid 204. The lid 204 is retained on the body 202 by one or more latches 206, e.g., a pivotable element that engages a catch, where the pivotable element may be attached to either the body 202 or the lid 204 and the catch is formed on the other of the body 202 or lid 204. Further, the container 200 includes one or more handles 208 for lifting, carrying, or otherwise handling the container 200. For example, a first handle 208 may be attached to a first end 202a of the body 202, as illustrated in FIGS. 20 and 21, and a second handle 208 may be attached to a second end 202b of the body 202, where the second end 202b is opposite the first end 202a. In other embodiments, a first handle 208 may be attached to a first side 202c of the body 202, and a second handle 208 may be attached to a second side 202d of the body 202, where the second side 202d is opposite the first side 202c and the first and second sides 202c, 202d extend between the first and second ends 202a, 202b. Other configurations and/or placements of one or more handles 208 may be used as well. Additionally, it will be appreciated that the sterilization container 100 may generally have the form of a parallelepipedal box shape as shown in FIG. 20, and the container 300 may have any appropriate size for containing the article(s) to be sterilized.

As further depicted in FIGS. 20 and 21, a visual seal indicator 210 provides a visual indication of a seal state of the sterilization container 200. For instance, the seal indicator 210 has a first indicator state and a second indicator state. In the first indicator state, the indicator 210 indicates to a user of the container 100 that the container 200 is in a first seal state, where the container 200 is not sealed against an ingress of contaminants (i.e., contaminants could enter the container 200). In the second indicator state, the indicator 210 indicates to the user that the container 100 is in a second seal state, where the container 200 is sealed against the ingress of contaminants (i.e., contaminants cannot enter the container 200). The first seal state also may be referred to as the unsealed state of the container 200, and the second seal state also may be referred to as the sealed state of the container 200. As such, the seal indicator 210 is a binary indicator of a change in state of a seal 220 of the container 100, e.g., when the seal is established and when the seal is broken or otherwise changes in pressure. As described herein, the seal indicator 210 is configured such that the seal indicator 210 is unaffected by the sterilization modality to which the container 200 is subjected to sterilize the articles within the container 200. The seal indicator 210 is described in greater detail herein.

Turning to FIGS. 22 and 23, schematic cross-section views are provided of the sterilization container 200. As shown, the container body 202 has a top lip 212 around its perimeter, and the lid 204 defines a groove 214 around its perimeter. The groove 214 has an inner groove surface 216. The top lip 212 defines a bottom sealing surface 218 and the inner groove surface 216 forms a top sealing surface. A seal 220 extends from the bottom sealing surface 218 to the top sealing surface, or inner groove surface, 216, i.e., the seal 220 extends within the groove 214 in contact with the top lip 212 and the inner groove surface 216. The seal 220 also is in contact with the side walls 215 of the groove 214, such that the top lip 212, inner groove surface 216, and side walls 215 help support the seal 220. Further, it will be appreciated that the seal 220 extends fully around the perimeter of the body 202 and the perimeter of the lid 204 and that the seal 220 is an air tight seal.

In the depicted exemplary embodiment, the seal 220 is an inflatable tube type seal or gasket that is manually inflated using a pump 260. The pump 260 includes a depressible membrane 262 overlying a depression 264 to define a cavity 266, i.e., the cavity 266 is defined in part by the membrane 262 and in part by the depression 264. When the membrane 262 is depressed, fluid (e.g., air) within the cavity 266 is displaced to one or more conduits 268, through which the fluid is conveyed to and received within the seal 220 to inflate the seal 220. Releasing the membrane 262 (i.e., such that the membrane 262 is no longer depressed) draws fluid into the cavity 266, which may be displaced to the seal 220 upon a successive depression of the membrane 262. That is, the pump 260 is a one-way pump for providing fluid to the seal 220 to pressurize the seal and thereby seal the container 200. When a sufficient amount of fluid is received within the seal 220, the sterilization container 200 is in a sealed state, where the container 200 is sealed against an ingress of contaminants such that contaminants cannot enter an interior or sterile space 226 of the container 200. Whether a sufficient amount of fluid is within the seal 220 may be indicated by the seal indicator 210, which indicates whether the container 200 is or is not properly sealed. In some embodiments, the pump 260 may be a single-use pump, e.g., the membrane 262 may remain depressed when the seal 220 has been properly pressurized such that the pump 260 cannot be used to direct any more air into the seal 220.

As illustrated in FIGS. 22 and 23, the depression 264 may be defined in a pump insert 270 that is attached or secured to the container body 202 such that the pump 260 is in fluid communication with the seal 220. Alternatively, the depression 264 may be defined in thickened portion of the body 202, e.g., the pump 260 may be located on a wall of the container body 202 that has a thickness sufficient to form the depression 264 without disrupting a plane of the inner surface of the wall (i.e., the surface of the wall within an interior of the container 200 is substantially planar). The thickness of the container body wall in which the depression 264 is defined may be the same as or greater than the thickness of one or more of the other walls of the container body 202.

Further, in some embodiments, the membrane 262 when depressed may bend or otherwise deform until the membrane 262 contacts the surface defining the depression 264. In other embodiments, the membrane 262 and depression 264 may be configured such that the membrane 262 does not contact the surface defining the depression 264, even when the membrane 262 is fully depressed. Still further, the pump insert 270 or container body 202 may include a flap, cover, or other feature that may be drawn or positioned over the pump 260 when the pump 260 is not in use, e.g., to prevent inadvertent depressions of the membrane 262, damage to the pump 260, etc.

It will be appreciated that the seal 220 is inflated and the sealed state established before the sterilization container 200 undergoes a sterilization process or protocol and is configured to remain sealed until a user opens the container 200 to retrieve one or more sterile items from within the container 200. That is, once the seal 220 is properly inflated, it remains sealed during and after the sterilization process, until the seal is intentionally broken. However, it is understood that, from time to time, the seal is lost or broken prior to when a user opens the container lid 204. For example, the inflatable tube type seal 220 may be damaged such that the fluid used to inflate the seal 220 seeps out of the seal 220 over time and the seal between the lid 204 and body 202 is eventually lost or broken. The seal indicator 210 is configured to indicate a second, unsealed state when the seal is lost or broken, in addition to indicating the second, unsealed state when the seal 220 has not been properly inflated.

As shown in FIGS. 20 through 23, the seal indicator 210 may be provided in proximity to the pump 260. For example, the seal indicator 210 is vertically above the pump 260 in the depicted embodiment. Further, in embodiments in which the pump 260 is part of a pump insert 270, the seal indicator 210 may be part of the pump insert 270 or may be visible through the pump insert 270. The indicator 210 may indicate the seal state of the sterilization container 200, e.g. a first seal state in which the container 200 is not sealed against contaminants (i.e., contaminants could enter the container 200) and a second seal state in which the container 200 is sealed against contaminants (i.e., contaminants cannot enter the container 200), through one or more windows 228 defined in the pump insert 270 (in embodiments comprising a pump insert 270), the container body 202, or the container lid 204. That is, the seal indicator 210 may be internal to either the pump insert 270 or the sterilization container 200, and the seal state indicated by the seal indicator 210 is visible through the window 228, which is defined either in the pump insert 270, the container body 202, or the container lid 204.

Moreover, in some embodiments, the visual indicator assembly 130 as described with respect to FIGS. 14 through 19 may be used with the sterilization container 200 to indicate whether the seal 220 is or is not properly sealed. In such embodiments, the seal indicator 210 is the same as the seal indicator 110 described above. Further, the visual indicator assembly 130 includes the other components previously described as part of the assembly 130.

In other embodiments, the visual indicator assembly may be configured differently than as described above and may be referred to as visual indicator assembly 280. That is, the seal indicator 210 comprises a visual indicator assembly 280 for actuating the seal indicator 210 between the first seal state and the second seal state. In one embodiment, the visual indicator assembly 280 comprises a plunger 282 that translates horizontally with a change in pressure of the seal 220 to transition between indicating the unsealed state of the container 200 and indicating the sealed state of the container 200. For example, as the pressure increases within the conduit(s) 268 and seal 220 as the pump 260 is used to inflate the seal 220, the plunger translates horizontally to transition from indicating the unsealed state to indicating the sealed state. More specifically, depressing the membrane 262 of the pump 260 displaces a fluid such as air into the conduit(s) 268 and seal 220, which increases the pressure in the conduit(s) 268 and seal 220. The plunger 282 is in fluid communication with the conduit(s) 268 and/or the seal 220, i.e., a pressurized portion of the container 200, such that the increased pressure in the pressurized portion causes the plunger 282 to move horizontally. Similarly, if the seal 220 is breached such that the pressure decreases, the plunger may translate horizontally to transition from indicating the sealed state to indicating the unsealed state. A biasing member, such as a spring, may be used to bias the plunger 282 to a default position or to help urge the plunger 282 horizontally to a new position as the pressure increases.

The plunger 282 may be dual colored such that as the plunger 282 translates horizontally, a color visible through the window 228 changes from a first color to a second color. A first color 282a of the dual colored plunger 282 indicates the first seal state and a second color 282b of the dual colored plunger 282 indicates the second seal state. More particularly, when the sterilization container 200 is not sealed against the ingress of contaminants, the seal indicator 210 displays the first color 282a in the window 228. That is, only a portion of the plunger 282 is visible in the window 228 such that a single color may be displayed in the window 228. Likewise, when the sterilization container 200 is sealed against the ingress of contaminants, the seal indicator 210 displays the second color 282b in the window 228. Accordingly, by viewing the plunger 282 through the window 228, a user can relatively quickly ascertain whether the sterilization container 200 is sterile or not sterile, or more specifically, the user can determine whether the contents of the container 200 are or are not sterile.

In another embodiment, the visual indicator assembly 280 comprises the plunger 282 that translates horizontally as the pump 260 is used to pressurize the seal 220, as well as an indicator segment 238 in operative communication with the plunger 282 and visible through the window 228. As the plunger 282 moves in response to pressure changes, the plunger 282 contacts the indicator segment 238 and moves the indicator segment 238 to change the seal state indicated by the indicator segment 238. More specifically, as described above with respect to the indicator segment 138 and the dual colored plunger 282, the indicator segment 238 may be dual colored such that as the indicator segment 238 is moved by the plunger 282, a color visible through the window 228 changes from a first color to a second color. A first color 238a of the dual colored indicator segment 238 indicates the first seal state and a second color 238b of the dual colored indicator segment 238 indicates the second seal state. More particularly, when the sterilization container 200 is not sealed against the ingress of contaminants, the seal indicator 210 displays the first color 238a in the window 228. That is, only a portion of the indicator segment 238 is visible in the window 228 such that a single color may be displayed in the window 228. Likewise, when the sterilization container 200 is sealed against the ingress of contaminants, the seal indicator 210 displays the second color 238b in the window 228. Therefore, as previously described, the indicator segment 238 visible through the window 228 can relatively quickly inform a user whether the sterilization container 200 is sterile or not sterile, or more specifically, the user can determine whether the contents of the container 200 are or are not sterile.

Although described above as a horizontally translating plunger, it will be appreciated that, in other embodiments, the plunger 282 may translate vertically rather than horizontally. In such embodiments, the plunger 282 may be dual colored and visible through the window 228 as previously described to inform a user of the container 200 of the seal state of the container 200. Alternatively, the vertically translating plunger 282 may be in operative communication with an indicator segment 238, which indicates the seal state of the container 200 to a user through the window 228. The visual indicator assembly 280 may have other configurations as well.

Further, it will be understood that, rather than a dual colored plunger 282 or dual colored indicator segment 238, the seal indicator 210 may comprise other features for indicating the seal state of the container 200. As an example, rather than being dual colored, the plunger 282 or indicator segment 238 may have two different visual patterns thereon, and a first pattern may be displayed when the container 200 is in the first seal state (i.e., unsealed), and a second pattern may be displayed when the container 200 is in the second seal state (i.e., sealed). Other visual indicia, e.g., images, color differences, words, etc., and other types of indicators 110, such as auditory or other non-visual indicators, may be used as well.

Moreover, in some embodiments, each sterilization container 100, 200 may include a system that compensates for a loss of pressure over time. For example, each of seal 120 and seal 220 may be configured to maintain its seal over a certain change in pressure (e.g., a given percentage decrease in the seal's internal pressure), and in some embodiments, the respective container 100, 200 may have one or more features that enable its seal 120, 220 to maintain its effectiveness over time. Such feature(s) may compensate for pressure loss over an indefinite period of time. In other embodiments, the container 100, 200 may be understood to have a limited shelf life, e.g., such a pressure compensation system may be omitted or may be effective only for a finite period of time. In such embodiments, the sterilization container 100, 200 may be marked, sorted, or the like such that a user can ascertain how much longer the contents of a given container 100, 200 should remain sterile.

Additionally, each sterilization container 100, 200 may be balanced such that small pressure changes that would otherwise occur (i.e., in an unbalanced system) may be reduced or eliminated. Balancing may reduce or eliminate the heat or steam impacts on the sterilization container 100, 200 and its seal 120, 220 as the container 100, 200 undergoes a sterilization process. Further, the seal indicator 110, 210 may be sealed or otherwise protected against impacts from the heat and/or steam of the sterilization process, e.g., to preserve the integrity of the seal indicator 110, 210 such that it continues to indicate the proper seal state of the container 100, 200. In still further embodiments, the sterilization container 100, 200 may include tamper evidence to alert a user that the container 100, 200 has been tampered with or has been used and/or tamper prevention to prevent tampering with the container 100, 200. For instance, a break-away tamper tag may be provided with the container 200 that is inserted into the pump cavity 266; when broken away, the tamper tag indicates the container 200 has been used. Other tamper evidence and/or prevention features may be provided with the sterilization container 100, 200.

Accordingly, with respect to the embodiments illustrated in FIGS. 11 through 23, the present subject matter provides sterilization containers with features for sealing against an ingress of contaminants such that each container remains sealed during and after undergoing a sterilization process or protocol. For instance, the container may include a gasket, e.g., a channeled gasket, or a pair of gaskets with a space in which a vacuum is pulled when the container undergoes sterilization to seal the container. As another example, the container may include a pump that is used to inflate a seal, e.g., a gasket, to seal the container; the pump may be a manual pump in which a membrane is depressed by a user to displace a fluid such as air into the seal. Moreover, each sterilization container includes a visual indicator for indicating a seal state of the container. For example, the visual indicator may be a binary indicator that displays either a first indicia or a second indicia through a window, e.g., defined in a body of the container. The first indicia may indicate a first seal state of the container, e.g., an unsealed state where contaminants could enter an interior of the container. The second indicia may indicate a second seal state of the container, e.g., a sealed state where contaminants cannot enter the interior of the container. The first and second indicia may be a first color and a second color, a first image and a second image, a first pattern and a second pattern, etc. The sterilization containers and visual indicators described herein provide containers for sterilizing items, such as medical instruments or the like, that may be sealed against an ingress of contaminants, may retain their seal, and may easily communicate to a user of the container whether the container is or is not properly sealed. Other advantages of the present subject matter also may be apparent to one of ordinary skill in the art.

The present subject matter also provides methods for indicating the integrity of a gasket of a sterilization container. For example, an exemplary method comprises providing a container body and a container lid that together define an interior for receipt of articles for sterilization. The container body has an open top portion, and the container lid covers the open top portion to close the sterilization container. The method also comprises providing a gasket that extends between the container body and the container lid when the container lid is positioned on the container body to seal the interior against an ingress of contaminants. Exemplary container bodies, lids, and gaskets are described with respect to the various sterilization container embodiments 10, 100, 200 discussed herein.

Further, the method comprises providing a seal indicator for indicating a seal state of the sterilization container. The seal indicator has a first indicium and a second indicium. The method also comprises displaying the first indicium when the sterilization container is in an unsealed state and displaying the second indicium when the sterilization container is in a sealed state. The seal indicator is visible to a user of the sterilization container such that the second indicium is not visible to the user in the unsealed state and the first indicium is not visible to the user in the sealed state. Moreover, in some embodiments, displaying the second indicium comprises displacing the seal indicator from a first position to a second position. Exemplary seal indicators are described with respect to the various sterilization container embodiments 10, 100, 200 discussed herein. In addition, modifications or extensions of the exemplary method also may be realized from the sterilization container embodiments and other subject matter discussed herein.

Additionally, although not described above with respect to every sterilization container embodiment 10, 100, 200, it will be appreciated that each sterilization container includes means for a sterilant to enter the container interior to sterilize any articles within the container. For example, vents or openings, as shown in the lids of the container embodiments 10, 100, 200 (e.g., in FIGS. 1, 3, 5, 6, 11, 20, 22, and 23), allow fluids, including a sterilant such as steam or a chemical agent, to pass into the sterilization container to sterilize any articles within the container interior. Further, as described herein, the vents or openings allow fluids to pass from the container interior to the exterior, e.g., to help dry or aerate the articles as the sterilant evaporates or degases. As further described herein, the seal indicators may be configured such that the sterilization modality, including the sterilant used in the sterilization process, does not affect the seal indicator. For example, the sterilization modality does not cause the seal indicator to transition from displaying a first indicium to displaying a second indicium; as a particular example, the sterilization modality does not cause the seal indicator to change color. However, in some embodiments, the sterilization modality may help establish the seal between the container lid and container body and a portion of the sterilization process (such as elevated temperature or pressure) may cause the seal indicator to transition from one indicator state to another based on the establishment of the container seal. In such embodiments, the seal indicator may be indirectly affected by the sterilization modality, although the seal indicator does not transition between indicator states based solely on the sterilization modality but, rather, in response to the effect of the sterilization modality on the container seal.

Moreover, it will be appreciated that, although not described above with respect to every sterilization container embodiment 10, 100, 200, the materials of each component of the container are selected to be compatible with the sterilization modality to which the container is subjected. For instance, the container body, container lid, and container gasket are each formed from a material that is compatible with the sterilization conditions to which the container will be submitted or vice versa, the sterilization conditions for a given container are selected to be within a range compatible with the material capabilities of the container materials. For example, the body and lid of each container 10, 100, 200 can be reusable and can be formed from a rigid material such stainless steel, anodized aluminum, polyetheretherketone (PEEK), polyaryletherketone, polyphenylsulphone (PPSU), polysulphone (PSU), filled PPSU, and filled PSU. Once sealed, as described in greater detail herein, the container can then be transferred to sterilizing equipment and exposed to sterilization conditions as generally known in the art. Such sterilization conditions can include, for example, steam, ethylene oxide, or hydrogen peroxide plasma sterilization conditions. Sterilization conditions are the conditions present during a particular sterilization methodology utilized that substantially kills or completely destroys bacteria and other infectious organisms in an industrial or medical product to the desirable sterility assurance level (e.g., $\geq 10^{-6}$ log reduction for terminal sterilization). The compatibility of the container materials with the sterilization modality may be one way in which the seal indicator of the container is unaffected by the sterilization modality. That is, the seal indicator materials may be selected such that the indicator is not induced to transition between indicia based on the sterilization conditions but based on whether the seal between the lid and body is established or broken.

Also, although not described above with respect to every sterilization container embodiment 10, 100, 200, it will be understood that one or more tags, such as tamper evidence tags and/or contents labels, may be included with each sterilization container. For example, a single use tamper evident tag, which breaks upon opening, may be attached to each sterilization container when the container is sealed. In one embodiment, a tamper evident tag includes a plastic flap across the interface between the container body and lid that tears upon opening. Additionally or alternatively, other tags or labels may be included with each sterilization container described herein. For instance, each container may include a label that, e.g., specifies the contents of the container, the date and time of sterilization, and/or other pertinent information, or a way to access such information, such as a radio-frequency identification (RFID) tag, a barcode, a matrix or two-dimensional barcode (or Quick Response (QR) code), or other appropriate means for accessing such information.

Further, it will be appreciated that the sterilization containers described herein may be configured to stack on top of one another or other containers. For example, the lids of the sterilization containers may provide rigidity, stability, and/or protection for the filter media such that the containers may be stacked. In addition, in some embodiments, particularly where the filter media is disposed between the lid and body and supports the lid at least in part, the edges of the filter media may be reinforced to provide rigidity for stacking. Moreover, the containers may include features for keeping space between the containers when stacked such that sterilant and/or evaporating fluids can enter and/or exit the containers through the vents. That is, the containers may be configured such that the vents are not blocked when one container is stacked on top of another.

Additionally, the sterilization containers described herein may include a second lid or cover that fits over the lids described herein, e.g., to prevent intrusions through the vent openings defined in the top of the lid. For example, it will be appreciated that contaminants or other debris matter could fall through the vent openings illustrated in the exemplary embodiments of the present subject matter, and such contaminants could fall into the container via a compromised filter or when the container is opened, thus compromising the sterility of the articles within the container. A particular example, an instrument end or the like could enter the vent openings, e.g., if the instrument is dropped on the lid, and thereby pierce, puncture, cut, tear, etc. the filter media that is positioned between the vent openings and the container interior, which could compromise the integrity of the filter and thereby could compromise the sterility of the articles within the container. Therefore, a second lid or cover may be provided to shield the vent openings defined in the exemplary lids described herein. The second lid or cover may be releasably attached to the lid or may be durably attached to the lid. Further, the second lid or cover may itself have define openings therein for fluids, such as the sterilant of the selected sterilization modality, to enter and exit the container. The defined openings of the second lid or cover are judiciously shaped and sized to ensure the desired Volume to Vent (V-to-V) ratio is maintained. It will be appreciated that such openings may be defined in the second lid or cover such that such openings do not face the same breach potential as the vent openings in the underlying lid. Alternatively or additionally, a gap may be defined between the second lid or cover and the underlying lid, e.g., around the outer perimeter of the lid, such that fluids may enter and exit the container via the gap between the lid and the second lid or cover. The second lid or cover may have other configurations as well, and in some embodiments, such a protective lid or cover may be unnecessary or undesirable and, thus, may be omitted.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization container, comprising:
   a body;
   a lid, the body and lid together defining an interior;
   a gasket for sealing the interior against an ingress of contaminants during and after a sterilization process;
   a seal indicator for indicating a seal state of the sterilization container, the seal indicator having a first indicator state that indicates an unsealed container state and a second indicator state that indicates a sealed container state,
   wherein the seal indicator is in the first indicator state when the gasket is not sufficiently compressed to seal the sterilization container against the ingress of contaminants during and after a sterilization process, and
   wherein the seal indicator is in the second indicator state when the gasket is sufficiently compressed to seal the sterilization container against the ingress of contaminants during and after a sterilization process; and
   a plurality of openings defined in a side or an end of the lid through which the seal indicator is visible to a user of the sterilization container,
   wherein each opening of the plurality of openings is a shaped orifice.

2. The sterilization container of claim 1, wherein the seal indicator displays a first indicium in the first indicator state and a second indicium in the second indicator state, and
   wherein the first indicium is a first color and the second indicium is a second color such that the seal indicator indicates a change in the seal state of the sterilization container through a change in color.

3. The sterilization container of claim 1, wherein the seal indicator is visible from an exterior of the sterilization container through an opening in the body.

4. The sterilization container of claim 1, wherein the seal indicator is visible from an exterior of the sterilization container through at least one opening of the plurality of openings in the lid.

5. The sterilization container of claim 1, wherein the gasket extends between the body and the lid to seal the interior against the ingress of contaminants.

6. The sterilization container of claim 5, wherein the gasket extends about a perimeter of the body and the lid.

7. The sterilization container of claim 1, wherein the body includes a first end, a second end opposite the first end, a first side extending between the first and second ends, and a second side extending between the first and second ends opposite the first side,
   wherein the seal indicator is visible from each of the first end, the second end, the first side, and the second side.

8. The sterilization container of claim 1, wherein the gasket is the seal indicator, and
   wherein the gasket comprises a first indicium to indicate the first indicator state and a second indicium to indicate the second indicator state.

9. The sterilization container of claim 8, wherein the gasket is made from a deformable material molded in two different colors, and
   wherein a first color of the two different colors is the first indicium and a second color of the two different colors is the second indicium.

10. The sterilization container of claim 1, wherein the seal indicator comprises a plunger extending between the gasket and an indicator segment, the plunger configured to contact the indicator segment when the plunger is displaced, and
    wherein the indicator segment includes a first indicium to indicate the first indicator state and a second indicium to indicate the second indicator state.

11. The sterilization container of claim 10, wherein the seal indicator further comprises a biasing member and a platform, the biasing member extending between a stop and the indicator segment, the platform on an end of the plunger opposite the indicator segment, and
    wherein, when the gasket is compressed, the gasket is configured to contact the platform and displace the plunger.

12. The sterilization container of claim 1, wherein the seal indicator comprises a stem, an indicator segment, and at least one bimetal washer,
    wherein the stem is positioned to contact the indicator segment, and
    wherein the at least one bimetal washer contacts the stem such that the at least one bimetal washer displaces the stem when the at least one bimetal washer deforms upon heating.

13. The sterilization container of claim 1, wherein the gasket is an inflatable tube, and
    wherein the seal indicator comprises a plunger that translates with a change in pressure of the gasket to transition between indicating the unsealed state and indicating the sealed state of the sterilization container.

14. The sterilization container of claim 1, further comprising:
    a manual pump for pressurizing the gasket to seal the sterilization container against the ingress of contaminants.

15. A method for indicating seal integrity of a gasket of a sterilization container during and after a sterilization process, the method comprising:
    providing a seal indicator for indicating a seal state of the sterilization container and a plurality of openings defined in a side or an end of a lid of the sterilization container through which the seal indicator is visible to a user of the sterilization container, the seal indicator having a first indicium and a second indicium, each opening of the plurality of openings being a shaped orifice;

displaying the first indicium when the sterilization container is in an unsealed state, wherein the unsealed state is when the gasket is not sufficiently compressed to seal the sterilization container against the ingress of contaminants during and after a sterilization process; and displaying the second indicium when the sterilization container is in a sealed state, wherein the sealed state is when the gasket is sufficiently compressed to seal the sterilization container against the ingress of contaminants during and after a sterilization process, wherein the seal indicator is visible to a user of the sterilization container such that the second indicium is not visible to the user in the unsealed state and the first indicium is not visible to the user in the sealed state.

16. The method of claim 15, further comprising:

providing a container body and a container lid that together define an interior for receipt of articles for sterilization, the container body having an open top portion, the container lid covering the open top portion to close the sterilization container.

17. The method of claim 16, wherein the gasket extends between the container body and the container lid when the container lid is positioned on the container body to seal the interior against an ingress of contaminants.

18. The method of claim 15, wherein displaying the second indicium comprises displacing the seal indicator from a first position to a second position.

19. A sterilization container, comprising:

a body;

a lid, the body and lid together defining an interior;

a combination gasket/filter having a gasket for sealing the interior against an ingress of contaminants integrally formed with filter media for forming a barrier between an external environment and the interior;

a seal indicator for indicating a seal state of the sterilization container, the seal indicator having a first indicator state that indicates an unsealed container state and a second indicator state that indicates a sealed container state, wherein the seal indicator is configured to display a first indicium in the first indicator state when the gasket is not sufficiently compressed to seal the sterilization container against the ingress of contaminants during and after a sterilization process, and wherein the seal indicator is configured to display a second indicium in the second indicator state when the gasket is sufficiently compressed to seal the sterilization container against the ingress of contaminants during and after a sterilization process; and a plurality of openings defined in a side or an end of the lid through which the seal indicator is visible to a user of the sterilization container, wherein each opening of the plurality of openings is a shaped orifice.

\* \* \* \* \*